US012781267B2

(12) United States Patent
Salaita et al.

(10) Patent No.: US 12,781,267 B2
(45) Date of Patent: Nov. 3, 2026

(54) DEVICES AND METHODS USEFUL FOR IMAGING TRANSIENT AND RARE MECHANICAL EVENTS IN CELLS

(71) Applicant: Emory University, Atlanta, GA (US)

(72) Inventors: Khalid Salaita, Atlanta, GA (US); Rong Ma, Atlanta, GA (US)

(73) Assignee: EMORY UNIVERSITY, Atlanta, GA (US)

( * ) Notice: Subject to any disclaimer, the term of this patent is extended or adjusted under 35 U.S.C. 154(b) by 1151 days.

(21) Appl. No.: 16/913,187

(22) Filed: Jun. 26, 2020

(65) Prior Publication Data

US 2021/0024985 A1 Jan. 28, 2021

Related U.S. Application Data

(60) Provisional application No. 62/879,343, filed on Jul. 26, 2019.

(51) Int. Cl.
*C12Q 1/6837* (2018.01)
*C12Q 1/6809* (2018.01)
*C12Q 1/6818* (2018.01)
*G01N 15/1433* (2024.01)

(52) U.S. Cl.
CPC ......... *C12Q 1/6837* (2013.01); *C12Q 1/6809* (2013.01); *C12Q 1/6818* (2013.01); *G01N 15/1433* (2024.01)

(58) Field of Classification Search
None
See application file for complete search history.

(56) References Cited

U.S. PATENT DOCUMENTS

| | | | | |
|---|---|---|---|---|
| 4,591,552 | A * | 5/1986 | Neurath | G01N 33/5761 435/7.92 |
| 5,429,922 | A * | 7/1995 | Sibley | C07K 14/45 435/6.15 |
| 5,837,832 | A * | 11/1998 | Chee | C07H 21/00 435/6.12 |
| 6,444,661 | B1 * | 9/2002 | Barton | C07F 15/008 514/288 |
| 8,859,233 | B2 * | 10/2014 | Larsen | A61P 37/04 435/449 |
| 9,260,762 | B2 * | 2/2016 | Winchell | C12Q 1/689 |
| 9,738,924 | B2 | 8/2017 | Bensimon | |
| 9,915,655 | B2 | 3/2018 | Bensimon | |
| 10,900,069 | B2 | 1/2021 | Salaita | |
| 2004/0067197 | A1 * | 4/2004 | Leclerc | A61K 51/0491 424/1.73 |
| 2004/0241651 | A1 * | 12/2004 | Olek | C07K 14/4703 435/6.16 |
| 2007/0160175 | A1 | 7/2007 | Lang | |
| 2009/0011943 | A1 * | 1/2009 | Drmanac | C12N 15/66 506/4 |
| 2009/0227043 | A1 | 9/2009 | Huang | |
| 2014/0255924 | A1 * | 9/2014 | Sampas | C12Q 1/6818 436/501 |
| 2014/0336071 | A1 * | 11/2014 | Salaita | G01N 33/542 422/69 |
| 2017/0037396 | A1 * | 2/2017 | Lee | C12N 15/113 |
| 2019/0002971 | A1 * | 1/2019 | Koslover | C12Q 1/6869 |
| 2019/0100732 | A1 * | 4/2019 | Hellman | C12N 15/62 |
| 2019/0219600 | A1 | 7/2019 | Salaita | |

FOREIGN PATENT DOCUMENTS

| | | | |
|---|---|---|---|
| WO | WO-9633207 A1 * | 10/1996 | C12N 15/10 |

OTHER PUBLICATIONS

Liu et al., "DNA-based nanoparticle tension sensors reveal that T-cell receptors transmit defined pN forces to their entigens for enhanced fidelity", Proceedings of the National Academy of Science, vol. 113, No. 20, pp. 5610-5615, May 17, 2016. (Year: 2016).*
Liu et al., "Molecular Tension Probes for Imaging Forces at the Cell Surface", American Chemical Society, 50, 2915-2924, 2017. (Year: 2017).*
"Oligonucleotide", Wikipedia.com, accessed Feb. 17, 2019. (Year: 2019).*
"Oligonucleotide definition," Merriam-Webster.com; accessed Aug. 23, 2017. (Year: 2017).*
Blakely et al. A DNA-based molecular probe for optically reporting cellular traction forces, Nat Methods, 2014, 11, 1229-1232.
Brockman et al. Mechanical Proofreading: A General Mechanism to Enhance the Fidelity of Information Transfer Between Cells, Front. Phys. 2019, 7:14.
Fang et al. Designing a Novel Molecular Beacon for Surface-Immobilized DNA Hybridization Studies, J. Am. Chem. Soc. 1999, 121, 2921-2922.
Liu et al. DNA-based nanoparticle tension sensors reveal that T-cell receptors transmit defined pN forces to their antigens for enhanced fidelity, PNAS 2016, 113 (20) 5610-5615.
Ma et al. DNA probes that store mechanical information reveal transient piconewton forces applied by T cells. PNAS, 2019, vol. 116 , No. 34, 16949-16954.
Massey et al. Time-Resolved Nucleic Acid Hybridization Beacons Utilizing Unimolecular and Toehold-Mediated Strand Displacement Designs, Anal. Chem. 2015, 87, 11923-11931.
Salaita et al. Restriction of Receptor Movement Alters Cellular Response: Physical Force Sensing by EphA2, Science 327, 1380 (2010).

(Continued)

*Primary Examiner* — Bradley L. Sisson

(57) ABSTRACT

In certain embodiments, this disclosure relates to devices and methods for imaging transient mechanical events in cells. In certain embodiments, this disclosure contemplates devices comprising receptors, cells or cell membranes comprising receptors, a molecular beacon as a linker between a solid surface and a ligand, and a locking oligonucleotide that selectively binds a portion of the hairpin turn and stem of the molecular beacon when the beacon is mechanically melted with piconewton forces. In certain embodiments, this disclosure relates to methods of locking, unlocking, and imaging cellular events using labeled locking and unlocking oligonucleotides disclosed herein.

10 Claims, 16 Drawing Sheets

Specification includes a Sequence Listing.

(56) References Cited

OTHER PUBLICATIONS

Stabley et al. Visualizing mechanical tension across membrane receptors with a fluorescent sensor, Nat Methods, 2011, 9(1):64-7.

Wang et al. Defining Single Molecular Forces Required to Activate Integrin and Notch Signaling, Science. 2013, 340(6135): 991-994.

Woodside et al. Nanomechanical measurements of the sequence-dependent folding landscapes of single nucleic acid hairpins, PNAS, 2006, 103 (16) 6190-6195.

Xiao et al. Hairpin DNA probes based on target-induced in situ generation of luminescent silver nanoclusters, Chem. Commun., 2014, 50, 4849.

Zhang et al. DNA-based digital tension probes reveal integrin forces during early cell adhesion, Nat Commun 5, 5167 (2014).

* cited by examiner

| sequence ID | description | sequence (5' to 3') |
|---|---|---|
| SEQ ID NO: 1<br>4.7 pN hp | hairpin strand in MTFM | GTG AAA TAC CGC ACA GAT GCG TTT GTA TAA ATG TTT TTT TCA TTT ATA CTTTAA GAG CGC CAC GTA GCC CAG C |
| SEQ ID NO: 7<br>A21B | top strand in MTFM | /5AmMC6/ - CGC ATC TGT GCG GTA TTT CAC TTT - /3Bio/ |
| SEQ ID NO: 7<br>Cy3B strand | Cy3B labeled A21B | Cy3B - CGC ATC TGT GCG GTA TTT CAC TTT - /3Bio/ |
| SEQ ID NO: 8<br>BHQ2 strand | bottom and quencher strand in MTFM | /5-ThioC6-5/ - TTT GCT GGG CTA CGT GGC GCT CTT - /3BHQ_2/ |
| SEQ ID NO: 9<br>scrambled 4.7 pN hp | scrambled hairpin strand in MTFM | GTG AAA TAC CGC ACA GAT GCG TTT GTA AAT ATG TGG TGG TCA TAT TTA CTT TAA GAG CGC CAC GTA GCC CAG C |
| SEQ ID NO:10<br>13mer | partial complement to 4.7 pN hp | AA AAC ATT TAT AC |
| SEQ ID NO:11<br>15mer | partial complement to 4.7 pN hp | AAA AAA CAT TTA TAC |
| SEQ ID NO: 6<br>17mer | partial complement to 4.7 pN hp | GAA AAA AAC ATT TAT AC |
| SEQ ID NO:12<br>21mer | partial complement to 4.7 pN hp | AAA TGA AAA AAA CAT TTA TAC |
| SEQ ID NO:13<br>25mer | full complement to 4.7 pN hp | GTA TAA ATG AAA AAA ACA TTT ATA C |
| SEQ ID NO:14<br>unstructured sequence | mimic 17mer binding site at hairpin open state | GT ATA AAT GTT TTT TTC CCA GCG TGA T /3THioMC3-D/ |
| 17mer locking strand (non-fluorescent) | complement to partial hairpin | GAA AAA AAC ATT TAT ACC CTA CCT A /3AmMO/<br>SEQ ID NO: 15 |
| 17mer locking strand | non-fluorescent locking strand | GAA AAA AAC ATT TAT ACC CTA CCT A-Atto647N<br>SEQ ID NO: 15 |

FIG. 6A

| sequence ID | description | sequence (5' to 3') |
|---|---|---|
| SEQ ID NO: 16 unlocking strand | full complement to locking strand (17 nt) | TAG GTA GGG TAT AAA TGT TTT TTT CGAA AA AAC ATT TAT ACC CTA CCT A-Atto647N |
| scrambled unlocking1 | 17mer region scrambled unlocking strand | TAG GTA GGC ACG CTG ATT AFT GTG G SEQ ID NO: 17 |
| scrambled unlocking2 | fully scrambled unlocking strand | TTA TCA TTG ACG CTG ATT AGT GTG G SEQ ID NO: 18 |

FIG. 6B

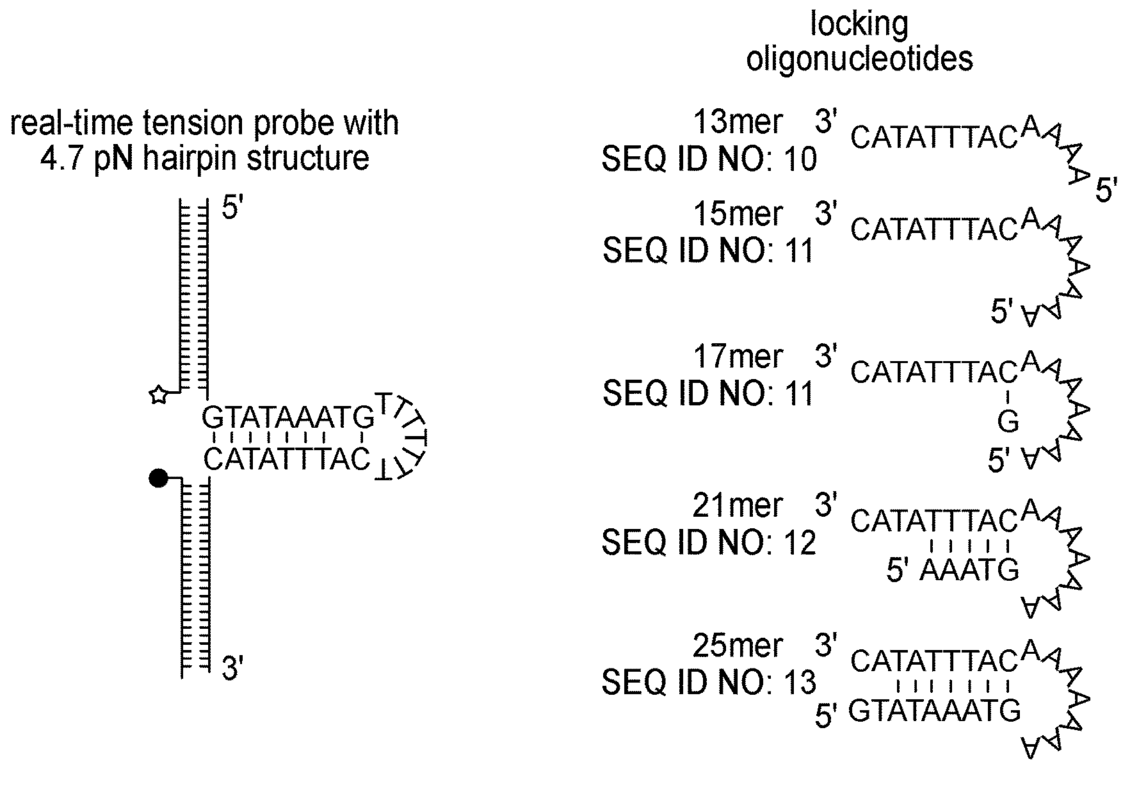

FIG. 7A

H1299 cancer cells on RGD
4.7 pN hairpin probe
15merHRP (1 μM, 10 min)

surface in solution

| SampleID | Count | Median: FL4-A |
|---|---|---|
| H1299 | 1649 | 29.5 |
| H1299 + SA647 | 4193 | 204 |
| H1299 + 15HRP + H2O2 + biotin-phenol + SA647 | 2678 | 171 |
| H1299 + HRP + H2O2 + biotin-phenol + SA647 | 719 | 134 |
| H1299 + 15HRP + biotin-phenol + SA647 | 3901 | 204 |
| H1299 + HRP + biotin-phenol + SA647 | 2635 | 165 |
| 4.7pN HP RGD wt H1299 + 15HRP + H2O2 + biotin-phenol + SA647 | 9148 | 11183 |
| 4.7pN HP RGD wt H1299 + HRP + H2O2 + biotin-phenol + SA647 | 7840 | 277 |
| 4.7pN HP wt H1299 + 15HRP + biotin-phenol + SA647 | 6705 | 54.6 |
| 4.7pN HP wt H1299 + HRP + biotin-phenol + SA647 | 7520 | 45.9 |

DEVICES AND METHODS USEFUL FOR IMAGING TRANSIENT AND RARE MECHANICAL EVENTS IN CELLS

CROSS-REFERENCE TO RELATED APPLICATIONS

This application claims the benefit of U.S. Provisional Application No. 62/879,343 filed Jul. 26, 2019. The entirety of this application is hereby incorporated by reference for all purposes.

STATEMENT REGARDING FEDERALLY SPONSORED RESEARCH OR DEVELOPMENT

This invention was made with government support under GM131099 and GM124472 awarded by the National Institutes of Health and 1350829 awarded by the National Science Foundation. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 19163US_ST25.txt. The text file is 5 KB, was created on Jun. 24, 2020, and is being submitted electronically via EFS-Web.

BACKGROUND

The interplay between physical inputs and chemical reaction cascades coordinates a diverse set of biological processes that range from epithelial cell adhesion and migration to stem cell differentiation and immune response. The majority of these mechanical inputs are sensed and transduced through membrane receptors that mount a signaling cascade depending on the mechanical properties of their specific cognate ligands. A major challenge to understanding the molecular mechanisms of mechanotransduction is in the development of tools that can be used to measure forces applied to specific receptors on the cell surface. Thus, there is a need to identify improved devices and methods.

Stabley et al. report visualizing mechanical tension across membrane receptors with a fluorescent sensor. Nature Methods, 2012, 9; 64-67.

Wang et al. report single molecular forces required to activate integrin and notch signaling. Science, 2013, 340 (6135):991-994.

Zhang et al. report DNA-based digital tension probes reveal integrin forces during early cell adhesion. Nat Commun, 2014, 5:5167.

Liu et al. report DNA-based nanoparticle tension sensors reveal that T-cell receptors transmit defined pN forces to their antigens for enhanced fidelity. Proc Natl Acad Sci USA, 2016, 113 (20): 5610-5615.

References cited herein are not an admission of prior art.

SUMMARY

This disclosure relates to devices and methods for imaging transient and rare mechanical events in cells. In certain embodiments, this disclosure contemplates devices comprising receptors, cells or cell membranes comprising receptors, a molecular beacon as a linker between a solid surface and a ligand, and a locking oligonucleotide that hybridizes to a portion of the hairpin turn and stem of the molecular beacon when the molecular beacon unravels or melts due to pulling forces on the ligand. In certain embodiments the locking oligonucleotide comprises a toehold segment. In certain embodiments, this disclosure relates to methods of locking, unlocking, and imaging cellular events using labeled locking oligonucleotides or toehold oligonucleotides disclosed herein. In certain embodiments, the label is horseradish peroxidase.

In certain embodiments, this disclosure contemplates using a locking oligonucleotide or toehold oligonucleotide to improve signal detection optionally in combination with erasing the signal using an unlocking nucleotide that binds the toehold segment. In certain embodiments, this disclosure contemplates using a locking oligonucleotide without a toehold segment when erasing the signal is not needed.

In certain embodiments, this disclosure contemplates a system comprising: a) a device comprising: i) a ligand; ii) a nucleic acid complex linker having a first end and a second end, wherein the nucleic acid complex linker is linked to the ligand at the first end; iii) a surface connected to the nucleic acid complex linker at the second end; wherein the nucleic acid complex linker comprises a hairpin motif comprising a double stranded stem segment, a single stranded loop segment, a first end tail segment, and a second end tail segment; and b) a locking oligonucleotide that hybridizes with the double stranded stem segment and the single stranded loop segment when a receptor binds the ligand and unravels or melts the hairpin motif providing an extended form derived from a single stranded motif.

In certain embodiments, this disclosure contemplates methods of detecting or imaging a receptor applying a pulling force on a ligand comprising a) mixing i) a receptor; ii) a device comprising, a nucleic acid complex linker having a first end and a second end, wherein the nucleic acid complex linker is linked to the ligand at the first end, and a surface connected to the nucleic acid complex linker at the second end; wherein the nucleic acid complex linker comprises a hairpin motif comprising a double stranded stem segment, a single stranded loop segment, a first end tail segment, and a second end tail segment; and iii) a locking oligonucleotide comprising a label that hybridizes with the double stranded stem segment and the single stranded loop segment when a receptor binds the ligand and unravels the hairpin motif providing an extended form derived from a single stranded motif; and b) detecting the label on the locking oligonucleotide. In certain embodiments, the label is a fluorescent molecule and detecting is observing the fluorescence of the label. In certain embodiments, the fluorescence is used to generate an image.

In certain embodiments, the label is horseradish peroxidase. In further embodiments, the methods comprise providing a device comprising a horseradish peroxidase labeled locking oligonucleotide and a conjugate comprising a phenol group and a second ligand with an oxidizing agent such as hydrogen peroxide under conditions to provide the receptor modified with the second ligand or a protein near the receptor modified with the second ligand. In certain embodiments, the second ligand is biotin or an antigen to an antibody. In certain embodiments, detecting the label includes mixing the device comprising the receptor modified with the second ligand and/or the protein near the receptor modified with the second ligand with a second receptor to the second ligand or an antibody to the antigen under conditions such that the second receptor, or nearby protein or antibody comprises a second label such as a fluorescent molecule and thereafter detecting, measuring, or imaging the fluorescence of the second label.

In certain embodiments, the label is redox active agent such as (N-(7-(dimethylamino)-3H-phenothiazin-3-ylidene)-N-methylmethanaminium) methylene blue. In further embodiments, the methods comprise providing a device comprising a redox active agent labeled locking oligonucleotide or methylene blue labeled locking oligonucleotide and detecting or measuring a current or peak current, shift, increase or decrease of the redox active agent or methylene blue with an electrode, e.g., with a potential in the range of −0.10 to −0.40 V (versus SCE) in pH 4-11.

In certain embodiments, this disclosure contemplates a system comprising: a) a device comprising: i) a ligand; ii) a nucleic acid complex linker having a first end and a second end, wherein the nucleic acid complex linker is linked to the ligand at the first end; iii) a surface connected to the nucleic acid complex linker at the second end; iv) a quencher conjugated to the nucleic acid complex linker wherein the quencher position remains static when the ligand moves; and v) a first fluorescent molecule conjugated to the nucleic acid complex linker wherein the fluorescent molecule is configured to move its position relative to the quencher when the ligand moves; wherein the nucleic acid complex linker comprises a hairpin motif comprising a double stranded stem segment, a single stranded loop segment, a first end tail segment, and a second end tail segment; wherein the quencher and the first fluorescent molecule are configured to quench when the nucleic acid complex linker is in the form of a hairpin motif; and wherein the quencher and the first fluorescent molecule are not configured quench when the nucleic acid complex linker is in the form of a single stranded motif; and b) a locking oligonucleotide that hybridizes with the double stranded stem segment and the single stranded loop segment.

In certain embodiments, the locking oligonucleotide comprises a label such as a fluorescent molecule when a receptor binds the ligand and unravels the hairpin motif providing an extended form derived from a single stranded motif.

In certain embodiments, the disclosure contemplates a nucleic acid complex linker configured such that it only binds a locking oligonucleotide when it is mechanically denatured. In certain embodiments, the nucleic acid complex linker is designed with a hidden (cryptic) binding segment to the locking oligonucleotide, i.e., locking oligonucleotide does not bind to the nucleic acid complex linker during static conditions; however, when the ligand moves, then the cryptic site is exposed, thus permitting the locking oligonucleotide to bind with the cryptic binding segment. The nucleic acid complex is configured to have mechanical selectively of at least or greater than 1:10 and in some cases this is 1:100 and 1:1000 or greater. Mechanical selectively is the ratio of the locking oligonucleotide binding to the cryptic segment with no ligand movement compared the locking oligonucleotide binding to the cryptic segment once the ligand moves and the nucleic acid complex linker melts due to pN forces.

In certain embodiments, devices and methods disclosed herein are capable of imaging ligand receptor forces at less than 100 pN, 50 pN, 10 pN or 5 pN and more than 4 pN or 1pN. In certain embodiments, devices and methods disclosed herein are capable of imaging ligand receptor forces that occur for less than 1 or 2 seconds.

In certain embodiments, this disclosure relates to devices comprising: i) a ligand; ii) a nucleic acid complex linker having a first end and a second end, wherein the nucleic acid complex linker is linked to the ligand at the first end; iii) a surface connected to the nucleic acid complex linker at the second end; iv) a quencher conjugated to the nucleic acid complex linker wherein the quencher position remains static when the ligand moves; v) a first fluorescent molecule conjugated to the nucleic acid complex linker wherein the fluorescent molecule is configured to move its position relative to the quencher when the ligand moves; and vi) a locking oligonucleotide comprising a sequence with only one nucleotide that base pairs with the last nucleotide of the double stranded stem segment followed by the reverse complement of the single stranded loop segment followed by the reverse complement of the double stranded stem segment; wherein the nucleic acid complex linker comprises a hairpin motif comprising a double stranded stem segment, a single stranded loop segment, a first end tail segment, and a second end tail segment; wherein the quencher and the first fluorescent molecule are configured to quench when the nucleic acid complex linker is in the form of a hairpin motif; wherein the quencher and the first fluorescent molecule are not configured quench when the nucleic acid complex linker is in the form of a single stranded motif.

In certain embodiments, this disclosure relates to devices comprising: i) a ligand; ii) a nucleic acid complex linker having a first end and a second end, wherein the nucleic acid complex linker is linked to the ligand at the first end; iii) a surface connected to the nucleic acid complex linker at the second end; iv) a first fluorescent molecule conjugated to the nucleic acid complex linker wherein the fluorescent molecule is configured to move its position relative to a quencher and/or the surface when the ligand moves. In certain embodiments, the device further comprises a quencher conjugated to the nucleic acid complex linker. In certain embodiments, the quencher is fixed relative to the surface, i.e., position remains static, when the ligand moves.

In certain embodiments, the nucleic acid complex linker comprises a hairpin motif comprising a double stranded stem segment, a single stranded loop segment, a first end tail segment, and a second end tail segment; wherein the first end tail segment hybridizes with a first tail segment complement conjugated to the first fluorescent molecule; wherein the second tail segment hybridizes with a second tail segment complement conjugated to the quencher; wherein the quencher and the first fluorescent molecule are configured to quench when the nucleic acid complex linker is in the form of a hairpin motif and the first end tail segment hybridizes with the first tail segment complement and when the second tail segment hybridizes with the second tail segment complement; and wherein the quencher and the first fluorescent molecule are not configured to quench when the nucleic acid complex linker is in the form of a single stranded motif and the first end tail segment hybridizes with the first tail segment complement and when the second tail segment hybridizes with the second tail segment complement.

In any embodiments disclosed herein, a quencher and a fluorescent molecule may be in reverse or opposite positions, i.e., a quencher may optionally be a fluorescent molecule and a fluorescent molecule may be a quencher. In any embodiments disclosed herein, the quencher may be absent, or the quencher may optionally be a fluorescent molecule, optionally of different excitation maximums and/or emission maximums in the case that two or more fluorescent molecules are used in the device or system. In certain embodiments, the excitation maximums and/or emission maximums differ by more than 50 nm, 100 nm, 150 nm, or 200 nm and optionally the excitation maximums and/or emission maximums differ by less than 150 nm, 200 nm or 400 nm. In certain embodiments, the nucleic acid complex linker does not contain a fluorescent molecule or quencher, or neither a fluorescent molecule nor a quencher.

In certain embodiments, devices further comprise a locking oligonucleotide or toehold oligonucleotide comprising a sequence with only one nucleotide that base pairs with the last nucleotide of the double stranded stem segment, adjacent to the single stranded loop, followed by the reverse complement of the single stranded loop segment followed by the reverse complement of the double stranded stem segment. In certain embodiments, the sequence with only one nucleotide that base pairs with the last nucleotide of the double stranded stem segment followed by the reverse complement of the single stranded loop segment followed by the reverse complement of the double stranded stem segment is between 16 and 18 nucleotides, or 15 and 19 nucleotide, or 15 and 20 nucleotides.

In certain embodiments, the locking oligonucleotide or toehold oligonucleotide comprises a 5' sequence consisting of GAAAAAAACATTTATAC (SEQ ID NO: 6). In certain embodiments, the locking oligonucleotide or toehold oligonucleotide is conjugated to a second fluorescent molecule wherein the first fluorescent molecule and second fluorescent molecule have different excitation maximums and/or emission maximums.

In certain embodiments, the ligand is conjugated to the first tail segment complement.

In certain embodiments, the surface is conjugated to the second tail segment complement.

In certain embodiments, the ligand is conjugated to the first tail segment.

In certain embodiments, the surface is conjugated to the second tail segment.

In certain embodiments, the surface is a gold nanoparticle.

In certain embodiments, the hairpin motif has the sequence (SEQ ID NO: 1)
(stem and loop segment in bold SEQ ID NO: 19)
GTGAAATACCGCACAGATGCGTTTGTATAAATGTTTTTTTCATTTATA
CTTTAAGAGCGCCACGTAGCCCAGC.

In certain embodiments, the double stranded stem segment has the sequence (SEQ ID NO: 2)
GTATAAATG.

In certain embodiments, the single stranded loop segment has the sequence (SEQ ID NO: 3)
TTTTTTT.

In certain embodiments, the first end tail segment has the sequence (SEQ ID NO: 4)
GTGAAATACCGCACAGATGC.

In certain embodiments, the second end tail segment has the sequence (SEQ ID NO: 5)
TTTAAGAGCGCCACGTAGCCCAGC.

In certain embodiments, this disclosure relates to methods of detecting a light signal from a cell receptor binding a ligand comprising the steps of: a) exposing a device disclosed herein to a cell containing a receptor to the ligand under conditions such that the device is connected to the cell membrane comprising the receptor of the ligand; and b) detecting the light signal. In certain embodiments, the light signals are used to create an image.

In certain embodiments, this disclosure relates to methods of detecting a light signal from a receptor binding a ligand comprising the steps of: a) exposing a device to a receptor to a ligand in the presence of a locking oligonucleotide; wherein the device comprises: i) a ligand; ii) a nucleic acid complex linker having a first end and a second end, wherein the nucleic acid complex linker is linked to the ligand at the first end; iii) a surface connected to the nucleic acid complex linker at the second end; iv) a quencher conjugated to the nucleic acid complex linker; and v) a first fluorescent molecule conjugated to the nucleic acid complex linker wherein the fluorescent molecule is configured to move its position relative to the quencher when the ligand moves upon binding to the receptor; wherein the nucleic acid complex linker comprises a hairpin motif comprising a double stranded stem segment, a single stranded loop segment, a first end tail segment, and a second end tail segment; wherein the quencher and the first fluorescent molecule are configured to quench when the nucleic acid complex linker is in the form of a hairpin motif; wherein the quencher and the first fluorescent molecule are not configured to quench when the nucleic acid complex linker is in the form of a single stranded motif; and wherein the receptor binds and pulls the ligand away from the surface to unravel or melt the hairpin motif into the single stranded motif removing the first fluorescent molecule from proximity to the quencher producing a light signal and the locking oligonucleotide hybridizes to the single stranded motif under conditions such that the nucleic acid complex linker is locked in an extended form derived from the single stranded motif; and b) detecting the light signal.

In certain embodiments, the methods further comprise mixing the nucleic acid complex linker in the single stranded motif with a locking oligonucleotide or toehold oligonucleotide under conditions such that the nucleic acid complex linker is locked in an expanded form derived from the single stranded motif. In certain embodiments, the locking oligonucleotide or toehold oligonucleotide comprises a sequence that is only one nucleotide that base pairs with the last nucleotide of the double stranded stem segment followed by the reverse complement of the single stranded loop segment followed by the reverse complement of the double stranded stem segment. In certain embodiments, the locking oligonucleotide or toehold oligonucleotide comprises a 5' sequence consisting of GAAAAAAACATTTATAC (SEQ ID NO: 6). In certain embodiments, the locking oligonucleotide or toehold oligonucleotide is conjugated to a second fluorescent molecule wherein the first fluorescent molecule and second fluorescent molecule have different excitation maximums and/or emission maximums.

In certain embodiments, the methods further comprise the step of mixing the nucleic acid complex linker locked in an expanded form derived from a single stranded motif and a third oligonucleotide comprising a sequence that hybridizes with the toehold oligonucleotide, wherein mixing is under conditions such that the toehold oligonucleotide and the third oligonucleotide hybridize. In certain embodiments, the third oligonucleotide comprises a first segment and a second segment, wherein the first segment comprising a sequence that hybridizes with a toehold oligonucleotide and does not contain a sequence greater than two sequential nucleotides within the first tail segment complement of the nucleic acid complex linker, and the second segment comprises a sequence which is identical to the hairpin motif of the nucleic acid complex linker. In certain embodiments, the first segment of the third oligonucleotide has 50%, 60%, or 70% or more G or C nucleotides. In certain embodiments, the first segment of the third oligonucleotide comprises a sequence TAGGTAGG (SEQ ID NO: 21).

BRIEF DESCRIPTION OF THE DRAWINGS

FIG. 6A shows a table of oligonucleotides SEQ ID NO: 1 and SEQ ID NO: 6-15.

FIG. 6B shows a table of oligonucleotides SEQ ID NO: 16-18.

FIG. 7A shows an illustration of a tension probe (stem-loop region SEQ ID NO: 19) and locking oligonucleotides ranging from 13mer to 25mer (SEQ ID NO: 6 and 10-13)

DETAILED DISCUSSION

Figure 1A:
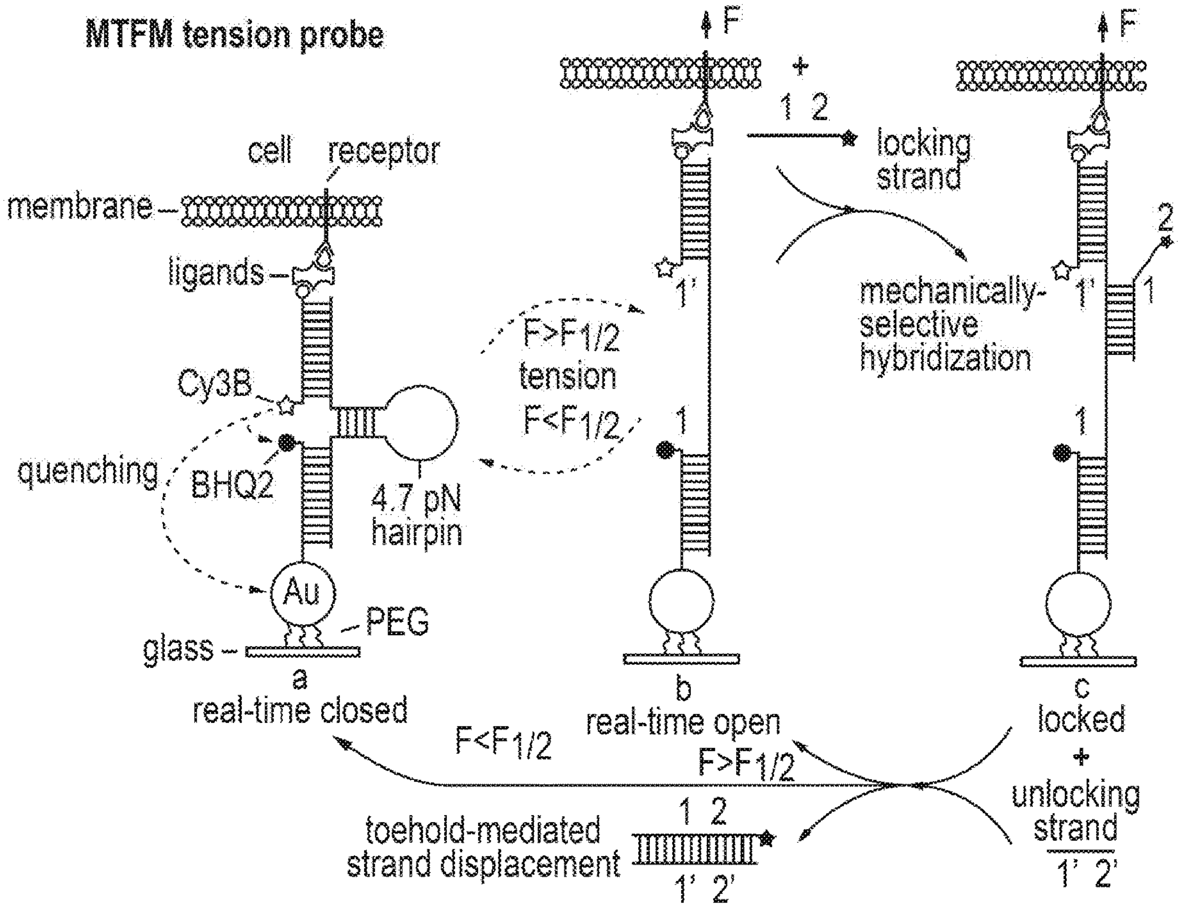
FIG. 1A shows a schematic depicting the concept of mechanical information storage.

Before the present disclosure is described in greater detail, it is to be understood that this disclosure is not limited to embodiments described, and as such may, of course, vary. It is also to be understood that the terminology used herein is for describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

As used in this disclosure and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") have the meaning ascribed to them in U.S. Patent law in that they are inclusive or open-ended and do not exclude additional, unrecited elements or method steps. The term "comprising" in reference to an oligonucleotide having a nucleic acid sequence refers to an oligonucleotide that may contain additional 5' (5' terminal end) or 3' (3' terminal end) nucleotides, i.e., the term is intended to include the oligonucleotide sequence within a larger nucleic acid. "Consisting essentially of" or "consists of" or the like, when applied to methods and compositions encompassed by the present disclosure refers to compositions like those disclosed herein that exclude certain prior art elements to provide an inventive feature of a claim, but which may contain additional composition components or method steps, etc., that do not materially affect the basic and novel characteristic(s) of the compositions or methods, compared to those of the corresponding compositions or methods disclosed herein. The term "consisting of" in reference to an oligonucleotide having a nucleotide sequence refers an oligonucleotide having the exact number of nucleotides in the sequence and not more or having not more than a range of nucleotide expressly specified in the claim. For example, "5' sequence consisting of" is limited only to the 5' end, i.e., the 3' end may contain additional nucleotides. Similarly, a "3' sequence consisting of" is limited only to the 3' end, and the 5' end may contain additional nucleotides.

As used herein, the term "conjugated" refers to linking molecular entities through covalent bonds, or by other specific binding interactions, such as due to hydrogen bonding or other van der Walls forces. The force to break a covalent bond is high, e.g., about 1500 pN for a carbon to carbon bond. The force to break a combination of strong protein interactions is typically a magnitude less, e.g., biotin to streptavidin is about 150 pN. Thus, a skilled artisan would understand that conjugation must be strong enough to restrict the breaking of bonds in order to implement the intended results. In certain embodiments, the term conjugated is intended to include linking molecular entities that do not break unless exposed to a force of about greater than about 5, 10, 25, 50, 75, 100, 125, or 150 pN depending on the context.

As used herein, the terms "oligonucleotide" is meant to include nucleic acids, ribonucleic or deoxyribonucleic acid, mixtures, nucleobase polymers, or analog thereof. An oligonucleotide can include native or non-native bases. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. It will be understood that a deoxyribonucleic acid used in the methods or compositions set forth herein can include uracil bases and a ribonucleic acid can include a thymine base.

The term "nucleobase polymer" refers to nucleic acids and chemically modified forms with nucleobase monomers. In certain embodiments, methods and compositions disclosed herein may be implemented with a nucleobase polymers comprising units of a ribose, 2'deoxyribose, locked nucleic acids (1-(hydroxymethyl)-2,5-dioxabicyclo[2.2.1]heptan-7-ol), 2'-O-methyl groups, a 3'-3'-inverted thymidine, phosphorothioate linkages, or combinations thereof. In certain embodiments, the nucleobase polymer may be less than 100, 50, or 35 nucleotides or nucleobases.

Nucleobase monomers are nitrogen containing aromatic or heterocyclic bases that bind to naturally occurring nucleic acids through hydrogen bonding otherwise known as base pairing. A typical nucleobase polymer is a nucleic acid, RNA, DNA, or chemically modified form thereof. A nucleobase polymer may be single or double stranded or both, e.g., they may contain overhangs. Nucleobase polymers may contain naturally occurring or synthetically modified bases and backbones. In certain embodiments, a nucleobase polymer need not be entirely complementary, e.g., may contain one or more insertions, deletions, or be in a hairpin structure provided that there is sufficient selective binding.

With regard to the nucleobases, it is contemplated that the term encompasses isobases, otherwise known as modified bases, e.g., are isoelectronic or have other substitutes configured to mimic naturally occurring hydrogen bonding base-pairs, e.g., within any of the sequences herein U may be substituted for T, or T may be substituted for U. Examples of nucleotides with modified adenosine or guanosine include, but are not limited to, hypoxanthine, xanthine, 7-methylguanine. Examples of nucleotides with modified cytidine, thymidine, or uridine include 5,6-dihydrouracil, 5-methylcytosine, 5-hydroxymethylcytosine. Contemplated isobases include 2'-deoxy-5-methylisocytidine (iC) and 2'-deoxy-isoguanosine (iG) (see U.S. Pat. Nos. 6,001,983; 6,037,120; 6,617,106; and 6,977,161).

Nucleobase polymers may be chemically modified, e.g., within the sugar backbone or on the 5' or 3' ends. As such, in certain embodiments, nucleobase polymers disclosed herein may contain monomers of phosphodiester, phosphorothioate, methylphosphonate, phosphorodiamidate, piperazine phosphorodiamidate, ribose, 2'-O-methy ribose, 2'-O-methoxyethyl ribose, 2'-fluororibose, deoxyribose, 1-(hydroxymethyl)-2,5-dioxabicyclo[2.2.1]heptan-7-ol, P-(2-(hydroxymethyl)morpholino)-N,N-dimethylphosphon amidate, morpholin-2-ylmethanol, (2-(hydroxymethyl)morpholino) (piperazin-1-yl)phosphinate, or peptide nucleic acids or combinations thereof.

In certain embodiments, the nucleotide base polymer is single or double stranded and/or is 3' end capped with one, two, or more thymidine nucleotides and/or 5' end polyphosphorylated, e.g., di-phosphate, tri-phosphate.

In certain embodiments, the nucleobase polymer can be modified to contain a phosphodiester bond, methylphosphonate bond or phosphorothioate bond. The nucleobase polymers can be modified, for example, 2'-amino, 2'-C-allyl, 2'-fluoro, 2'-O-methyl, 2'-H of the ribose ring. Constructs can be purified by gel electrophoresis using general methods or can be purified by high pressure liquid chromatography and re-suspended in water.

In certain embodiments, nucleobase polymers include one or more (e.g., about 1, 2, 3, 4, 5, 6, 7, 8, 9, 10, or more) LNA "locked nucleic acid" nucleotides such as a 2',4'-C methylene bicyclo nucleotide (see for example U.S. Pat. Nos. 6,639,059, 6,670,461, 7,053,207).

In one embodiment, the disclosure features modified nucleobase polymers, with phosphate backbone modifications comprising one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl, substitutions.

As used herein, the term "ligand" refers to an organic molecule, i.e., substantially comprised of carbon, hydrogen, and oxygen, that binds a "receptor." Receptors are organic molecules typically found on the surface of a cell. Through binding a ligand to a receptor, the cell has a signal of the extra cellular environment which may cause changes inside the cell. As a convention, a ligand is usually used to refer to the smaller of the binding partners from a size standpoint, and a receptor is usually used to refer to a molecule that spatially surrounds the ligand or portion thereof. However as used herein, the terms can be used interchangeably as they generally refer to molecules that are specific binding partners. For example, a glycan may be expressed on a cell surface glycoprotein and a lectin may bind the glycan. As the glycan is typically smaller and surrounded by the lectin during binding, it may be considered a ligand even though it is a receptor of the lectin binding signal on the cell surface. In another example, a double stranded oligonucleotide sequence contains two complimentary nucleic acid sequences. Either of the single stranded sequences may be consider the ligand or receptor of the other. In certain embodiments, a ligand is contemplated to be a compound that has a molecular weight of less than 500 or 1,000. In certain embodiments, a receptor is contemplated to be a compound that has a molecular weight of greater than 2,000 or 5,000. In any of the embodiments disclosed herein the position of a ligand and a receptor may be switched.

As used herein, the term "surface" refers to the outside part of an object. The area is typically of greater than about one hundred square nanometers, one square micrometer, or more than one square millimeter. Examples of contemplated surfaces are on a particle, bead, wafer, array, well, microscope slide, transparent or opaque glass, polymer, or metal, or the bottom of a zero-mode waveguide. A "zero-mode waveguide (ZMW)" refers to a confined structure or chamber located in an opening, e.g., hole, of a metal film deposited on a transparent substrate. See Levene et al., Science, 2003, 299:682-686. The chamber acts as a wave guide for light coming out of the bottom of the opening. The openings are typically about 150-50 nm in width and depth. Due to the behavior of light when it travels through a small aperture, the optical field decays exponentially inside the chamber. Thus, fluorescent molecules will lose fluorescence as they move away from the bottom of the chamber.

As used herein, "subject" refers to any animal, preferably a human patient, livestock, or domestic pet.

Unless stated otherwise as apparent from the following discussion, it will be appreciated that terms such as "detecting," "receiving," "quantifying," "mapping," "generating," "registering," "determining," "obtaining," "processing," "computing," "deriving," "estimating," "calculating," "inferring" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods may be compiled for execution on a variety of hardware platforms and for interface to a variety of operating systems. In addition, embodiments are not described with reference to any particular programming language. It will be appreciated that a variety of programming languages may be used to implement embodiments of the disclosure.

In some embodiments, the disclosed methods may be implemented using software applications that are stored in a memory and executed by a processor (e.g., CPU) provided on the system. In some embodiments, the disclosed methods may be implanted using software applications that are stored in memories and executed by CPUs distributed across the system. As such, the modules of the system may be a general purpose computer system that becomes a specific purpose computer system when executing the routine of the disclosure. The modules of the system may also include an operating system and micro instruction code. The various processes and functions described herein may either be part of the micro instruction code or part of the application program or routine (or combination thereof) that is executed via the operating system.

It is to be understood that the embodiments of the disclosure may be implemented in various forms of hardware, software, firmware, special purpose processes, or a combination thereof. In one embodiment, the disclosure may be implemented in software as an application program tangible embodied on a computer readable program storage device. The application program may be uploaded to, and executed by, a machine comprising any suitable architecture. The system and/or method of the disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

It is to be further understood that, because some of the constituent system components and method steps depicted in the accompanying figures may be implemented in software, the actual connections between the systems components (or the process steps) may differ depending upon the manner in which the disclosure is programmed. Given the teachings of the disclosure provided herein, one of ordinary skill in the related art will be able to contemplate these and similar implementations or configurations of the disclosure.

Devices and Methods of Use

This disclosure relates to systems, devices, and methods for imaging transient and rare mechanical events in cells. In certain embodiments, this disclosure contemplates devices comprising receptors, cells or cell membranes comprising receptors, a molecular beacon as a linker between a solid surface and a ligand, and a locking oligonucleotide that hybridizes to a portion of the hairpin turn and stem of the molecular beacon when the molecular beacon unravels due to pulling forces on the ligand. In certain embodiments the locking oligonucleotide comprises a toehold segment. In certain embodiments, this disclosure relates to methods of locking, unlocking, and imaging cellular events using labeled locking oligonucleotides or toehold oligonucleotides disclosed herein.

In certain embodiments, the molecular beacon in the form of a nucleic acid linker complex folds into a stem loop structure, and this secondary structure "mechanically melts" when a ligand moves and a locking oligonucleotide preferentially binds the nucleic acid complex that is mechanically melted forming an expanded locked structure derived from the single stranded motif. In certain embodiments, this disclosure contemplates using a locking oligonucleotide or toehold oligonucleotide to improve signal detection optionally in combination with erasing the signal using an unlocking nucleotide that binds the toehold segment thereby erasing the signal. In certain embodiments, this disclosure contemplates using a locking oligonucleotide without a toehold segment when erasing the signal is not needed.

In certain embodiments, this disclosure contemplates a system comprising: a) a device comprising: i) a ligand; ii) a nucleic acid complex linker having a first end and a second end, wherein the nucleic acid complex linker is linked to the ligand at the first end; iii) a surface connected to the nucleic acid complex linker at the second end; wherein the nucleic acid complex linker comprises a hairpin motif comprising a double stranded stem segment, a single stranded loop segment, a first end tail segment, and a second end tail segment; and b) a locking oligonucleotide that hybridizes with the double stranded stem segment and the single stranded loop segment when a receptor binds the ligand and unravels or melts the hairpin motif providing an extended form derived from a single stranded motif.

In certain embodiments, this disclosure contemplates methods of detecting or imaging a receptor applying a pulling force on a ligand comprising a) mixing i) a receptor; ii) a device comprising, a nucleic acid complex linker having a first end and a second end, wherein the nucleic acid complex linker is linked to the ligand at the first end, and a surface connected to the nucleic acid complex linker at the second end; wherein the nucleic acid complex linker comprises a hairpin motif comprising a double stranded stem segment, a single stranded loop segment, a first end tail segment, and a second end tail segment; and iii) a locking oligonucleotide comprising a label that hybridizes with the double stranded stem segment and the single stranded loop segment when a receptor binds the ligand and unravels the hairpin motif providing an extended form derived from a single stranded motif; and b) detecting the label on the locking oligonucleotide. In certain embodiments, the label is a fluorescent molecule and detecting is observing the fluorescence of the label. In certain embodiments, the fluorescence is used to generate an image.

In certain embodiments, this disclosure contemplates a system comprising: a) a device comprising: i) a ligand; ii) a nucleic acid complex linker having a first end and a second end, wherein the nucleic acid complex linker is linked to the ligand at the first end; iii) a surface connected to the nucleic acid complex linker at the second end; iv) a quencher conjugated to the nucleic acid complex linker wherein the quencher position remains static when the ligand moves; and v) a first fluorescent molecule conjugated to the nucleic acid complex linker wherein the fluorescent molecule is configured to move its position relative to the quencher or the surface when the ligand moves; wherein the nucleic acid complex linker comprises a hairpin motif comprising a double stranded stem segment, a single stranded loop segment, a first end tail segment, and a second end tail segment; wherein the quencher and the first fluorescent molecule are configured to quench when the nucleic acid complex linker is in the form of a hairpin motif; and wherein the quencher and the first fluorescent molecule are not configured quench when the nucleic acid complex linker is in the form of a single stranded motif; and b) a locking oligonucleotide that hybridizes with the double stranded stem segment and the single stranded loop segment.

In certain embodiments, this disclosure relates to devices comprising: i) a ligand; ii) a nucleic acid complex linker having a first end and a second end, wherein the nucleic acid complex linker is linked to the ligand at the first end; iii) a surface connected to the nucleic acid complex linker at the second end; iv) a quencher conjugated to the nucleic acid complex linker wherein the quencher position remains static when the ligand moves; v) a first fluorescent molecule conjugated to the nucleic acid complex linker wherein the fluorescent molecule is configured to move its position relative to the quencher when the ligand moves; and vi) a locking oligonucleotide comprising a sequence with only one nucleotide that base pairs with the last nucleotide of the double stranded stem segment followed by the reverse complement of the single stranded loop segment followed by the reverse complement of the double stranded stem segment; wherein the nucleic acid complex linker comprises a hairpin motif comprising a double stranded stem segment, a single stranded loop segment, a first end tail segment, and a second end tail segment; wherein the quencher and the first fluorescent molecule are configured to quench when the nucleic acid complex linker is in the form of a hairpin motif; wherein the quencher and the first fluorescent molecule are not configured quench when the nucleic acid complex linker is in the form of a single stranded motif.

In certain embodiments, this disclosure relates to devices comprising: i) a ligand; ii) a nucleic acid complex linker having a first end and a second end, wherein the nucleic acid complex linker is linked to the ligand at the first end; iii) a surface connected to the nucleic acid complex linker at the second end; iv) a first fluorescent molecule conjugated to the nucleic acid complex linker wherein the fluorescent molecule is configured to move its position relative to a quencher and/or the surface when the ligand moves. In certain embodiments, the device further comprises a quencher conjugated to the nucleic acid complex linker. In certain embodiments, the quencher is fixed relative to the surface, i.e., position remains static, when the ligand moves.

In certain embodiments, the nucleic acid complex linker comprises a hairpin motif comprising a double stranded stem segment, a single stranded loop segment, a first end tail segment, and a second end tail segment; wherein the first end tail segment hybridizes with a first tail segment complement conjugated to the first fluorescent molecule; wherein the second tail segment hybridizes with a second tail segment complement conjugated to the quencher; wherein the quencher and the first fluorescent molecule are configured to quench when the nucleic acid complex linker is in the form of a hairpin motif and the first end tail segment hybridizes with the first tail segment complement and when the second tail segment hybridizes with the second tail segment complement; and wherein the quencher and the first fluorescent molecule are not configured to quench when the nucleic acid complex linker is in the form of a single stranded motif and the first end tail segment hybridizes with the first tail segment complement and when the second tail segment hybridizes with the second tail segment complement.

In any embodiments disclosed herein a quencher and a fluorescent molecule may be in reverse or opposite positions, i.e., a quencher may optionally be a fluorescent molecule and a fluorescent molecule may be a quencher.

In certain embodiments, devices further comprise a locking oligonucleotide or toehold oligonucleotide comprising a sequence with only one nucleotide that base pairs with the last nucleotide of the double stranded stem segment, adjacent to the single stranded loop, followed by the reverse complement of the single stranded loop segment followed by the reverse complement of the double stranded stem segment. In certain embodiments, the sequence with only one nucleotide that base pairs with the last nucleotide of the double stranded stem segment followed by the reverse complement of the single stranded loop segment followed by the reverse complement of the double stranded stem segment is between 16 and 18 nucleotides, or 15 and 19 nucleotide, or 15 and 20 nucleotides.

In certain embodiments, this disclosure relates to methods of detecting a light signal from a cell receptor binding a ligand comprising the steps of: a) exposing a device disclosed herein to a cell containing a receptor to the ligand under conditions such that the device is connected to the cell membrane comprising the receptor of the ligand; and b) detecting the light signal. In certain embodiments, the light signals are used to create an image.

In certain embodiments, this disclosure relates to methods of detecting a light signal from a receptor binding a ligand comprising the steps of: a) exposing a device to a receptor to a ligand in the presence of a locking oligonucleotide; wherein the device comprises: i) a ligand; ii) a nucleic acid complex linker having a first end and a second end, wherein the nucleic acid complex linker is linked to the ligand at the first end; iii) a surface connected to the nucleic acid complex linker at the second end; iv) a quencher conjugated to the nucleic acid complex linker; and v) a first fluorescent molecule conjugated to the nucleic acid complex linker wherein the fluorescent molecule is configured to move its position relative to the quencher when the ligand moves upon binding to the receptor; wherein the nucleic acid complex linker comprises a hairpin motif comprising a double stranded stem segment, a single stranded loop segment, a first end tail segment, and a second end tail segment; wherein the quencher and the first fluorescent molecule are configured to quench when the nucleic acid complex linker is in the form of a hairpin motif; wherein the quencher and the first fluorescent molecule are not configured quench when the nucleic acid complex linker is in the form of a single stranded motif; and wherein the receptor binds and pulls the ligand away from the surface to unravel the hairpin motif into the single stranded motif removing the first fluorescent molecule from proximity to the quencher producing a light signal and the locking oligonucleotide hybridizes to the single stranded motif under conditions such that the nucleic acid complex linker is locked in an extended form derived from the single stranded motif; and b) detecting the light signal.

In certain embodiments, the methods further comprise mixing the nucleic acid complex linker in the single stranded motif with a locking oligonucleotide or toehold oligonucleotide under conditions such that the nucleic acid complex linker is locked in an expanded form derived from the single stranded motif. In certain embodiments, the locking oligonucleotide or toehold oligonucleotide comprises a sequence that is only one nucleotide that base pairs with the last nucleotide of the double stranded stem segment followed by the reverse complement of the single stranded loop segment followed by the reverse complement of the double stranded stem segment. In certain embodiments, the locking oligonucleotide or toehold oligonucleotide comprises a 5' sequence consisting of GAAAAAAACATTTATAC (SEQ ID NO: 6). In certain embodiments, the locking oligonucleotide or toehold oligonucleotide is conjugated to a second fluorescent molecule wherein the first fluorescent molecule and second fluorescent molecule have different excitation maximums and/or emission maximums.

In certain embodiments, the methods further comprise the step of mixing the nucleic acid complex linker locked in an expanded form derived from a single stranded motif and a third oligonucleotide comprising a sequence that hybridizes with the toehold oligonucleotide, wherein mixing is under conditions such that the toehold oligonucleotide and the third oligonucleotide hybridize. In certain embodiments, the third oligonucleotide comprises a first segment and a second segment, wherein the first segment comprising a sequence that hybridizes with a toehold oligonucleotide and does not contain a sequence greater than two sequential nucleotides within the first tail segment complement of the nucleic acid complex linker, and the second segment comprises a sequence which is identical to the hairpin motif of the nucleic acid complex linker.

In certain embodiments, the first segment of the third oligonucleotide has 50%, 60%, or 70% or more G or C nucleotides. In certain embodiments, the first segment of the third oligonucleotide comprises a sequence TAGGTAGG (SEQ ID NO: 21).

In certain embodiments, the methods further comprise the step of mixing the nucleic acid complex linker locked in an extended form derived from a single stranded motif by exposure to a locking oligonucleotide or toehold oligonucleotide and a third oligonucleotide comprising a sequence that hybridizes with the toehold oligonucleotide, wherein mixing is under conditions such that the toehold oligonucleotide and the third oligonucleotide hybridize. In certain embodiments, the third oligonucleotide comprises a first segment and a second segment, wherein the first segment comprising a sequence that hybridizes with toehold oligonucleotide and does not contain a sequence greater than two sequential nucleotides within the first tail segment complement of the nucleic acid complex linker, and the second segment comprises a sequence which is identical to the hairpin motif of the nucleic acid complex linker.

In certain embodiments, this disclosure contemplates a device comprising: i) a ligand; ii) a nucleic acid complex linker having a first end and a second end, wherein the nucleic acid complex linker is linked to the ligand at the first end; iii) a zero-mode wave guide surface connected to the nucleic acid complex linker at the second end; and iv) a first fluorescent molecule conjugated to the nucleic acid complex linker wherein the fluorescent molecule is configured to move its position relative to the surface when the ligand moves, wherein the nucleic acid complex linker comprises a hairpin motif comprising a double stranded stem segment, a single stranded loop segment, a first end tail segment, and a second end tail segment; wherein the first end tail segment hybridizes with a first tail segment complement conjugated to the first fluorescent molecule; wherein the second tail segment hybridizes with a second tail segment complement; wherein the first fluorescent molecule is configured to produce a light signal when the nucleic acid complex linker is in the form of a hairpin motif and wherein the first fluorescent molecule is not configured to produce a weaker or lesser light signal when the nucleic acid complex linker is in the form of a single stranded motif or locked in an expanded form derived from the single stranded motif In certain embodiments, a fluorescence-based system may be used for detecting, visualizing and potentially measuring transient external cellular forces or cell/cell interactions in live cells. In certain embodiments, the disclosure relates to a device comprising a platform-bound ligand fused to two molecular entities: a fluorophore and a quencher are separated by a nucleic acid complex linker. In the absence of any binding, the fluorophore ligand conjugate is in close proximity to the quenching signal, and there is no fluorescence. Upon binding to a receptor or other interacting protein, the fluorophore ligand conjugate is pulled away from the platform by these proteins, thereby separating them spatially from the quencher, activating fluorescence. The farther the two are separated, the brighter the signal becomes. The strength of signal can also be correlated to the force exerted, allowing one to obtain a measure of the force exerted by the receptor on its ligand, a measure of the force of an interaction. To obtain this measurement, one can utilize software that takes the images or video and converts them into a force map, allowing users to detect the forces of this interaction anywhere in the cell.

In certain embodiments, the fluorophore ligand conjugate is replaced with a quencher ligand conjugate. The fluorophore is concurrently connected near the surface of the platform. Upon binding to a receptor or other interacting protein, the quencher ligand conjugate is pulled away from the platform by these proteins, thereby separating them spatially from the quencher, activating fluorescence near the surface of the platform.

In certain embodiments, the system may be used to detect cancer cells. Malignant cancer cells are typically “softer” than normal cells, as measured by their resistance to an externally applied force. Of note is that different types of cancer have differing resistances; thus, in one embodiment, the disclosure contemplates the use of systems disclosed herein to create a cancer diagnostic based upon the resistance signature of a cell or tissue.

In certain embodiments, the disclosure relates to a device comprising a ligand connected to a nucleic acid complex linker and a label that emits a signal. The signal varies with the distance of the label from a surface. A system is created when the ligand attaches to a cell receptor. The cell receptor can exert a force on the device, thereby moving the position of the label with respect to the surface and changing the signal.

In some embodiments, the label can include two fluorescent molecules. These fluorescent molecules can be (independent of one another) fluorescent dyes, quantum dots, fluorescent proteins, or any other similarly fluorescent molecule. One fluorescent molecule is configured to remain fixed (i.e., does not substantially move its position) relative to the location of the surface when the cell receptor exerts a force on the device, while the other fluorescent molecule is configured to move its relative position with respect to the surface. The change in position of one fluorescent molecule with respect to the other can cause the signal to change in a quantifiable manner. In some embodiments, the two fluorescent molecules can be chosen based on properties such that the fluorescence of one molecule is absorbed by the other molecule and then the other molecule fluoresces at a different wavelength. In some embodiments, one of the fluorescent molecules can be configured to act as a quencher, absorbing the fluorescence of the other molecule, but not emitting any fluorescence.

In certain embodiments, the disclosure relates to devices that comprise: a nucleic acid complex linker having a first end and a second end; a ligand conjugated about the first end of the nucleic acid complex linker; a first molecule conjugated about the first end; a surface conjugated to the second end of the molecular linker; and a second molecule conjugated about the surface, provided that at least one of the first or second molecules is a FRET donor and at least one of the first or second molecules is a FRET acceptor.

In certain embodiments, the first molecule is a fluorescent quencher to the second molecule. In certain embodiments, the second molecule is a fluorescent quencher to the first molecule. In certain embodiments, the donor and acceptor are the same, and FRET is detected by the resulting fluorescence depolarization.

In certain embodiments, FRET can be detected by the appearance of sensitized fluorescence of the acceptor or by quenching of donor fluorescence. Nonfluorescent acceptors such as dabcyl and QSY dyes are contemplated.

In certain embodiments, the first or second fluorescent molecule is a dye, quantum dot, or protein. In certain embodiments, the donor or acceptor molecule is selected from xanthene derivatives: fluorescein, rhodamine, Oregon green, eosin, Texas red, and Cal Fluor dyes, cyanine derivatives: cyanine, indocarbocyanine, oxacarbocyanine, thiacarbocyanine, merocyanine, and quasar dyes, naphthalene derivatives (dansyl and prodan derivatives), coumarin derivatives, oxadiazole derivatives: pyridyloxazole, nitrobenzoxadiazole and benzoxadiazole, pyrene derivatives: cascade blue, oxazine derivatives: nile red, nile blue, cresyl violet, oxazine 170, acridine derivatives: proflavin, acridine orange, acridine yellow, arylmethine derivatives: auramine, crystal violet, malachite green, tetrapyrrole derivatives: porphin, phthalocyanine, bilirubin, a CF dye (Biotium), a BODIPY (Invitrogen), a Alexa Fluor such a fluorophore is Alexa Fluor 350, Alexa Fluor 488, Alexa Fluor 546, Alexa Fluor 555, Alexa Fluor 568, Alexa Fluor 594, Alexa 647 (Invitrogen), a DyLight Fluor (Thermo Scientific, Pierce), an Atto and Tracy (Sigma Aldrich), a FluoProbes (Interchim), a MegaStokes Dye (Dyomics), QSY21, or other compounds disclosed herein.

In certain embodiments, the FRET donor acceptor pairs may be a fluorescein and a tetramethylrhodamine, IAEDANS and a fluorescein; EDANS and a dabcyl, a fluorescein and a fluorescein, a BODIPY FL and a BODIPY FL, a fluorescein and a QSY 7, QSY 9 dyes, QSY 21, or QSY 35, an Alexa Fluor and a QSY 7, QSY 9, QSY 21, QSY 35 dyes, or other compounds disclosed herein.

This disclosure relates to methods of detecting the presence of molecules and optionally quantifying forces associated with molecular interactions on the surface of cells and other lipids. In certain embodiments, the devices disclosed herein can be used to detect forces through cell surface receptors. In other embodiments, the devices can be used to detect the presence or absence of molecules on cells or other particles or detect the changes in cell morphology after ligand receptor binding.

In certain embodiments, the ligand is a biological molecule, protein, protein fragment, nucleic acid, glycoprotein, polysaccharide, hormone, steroid, therapeutic agent, or other molecule with affinity for a protein or receptor. In certain embodiments, the surface is a particle, bead, wafer, array, well, microscope slide, transparent or opaque glass or polymer, or bottom of a zero-mode waveguide.

In certain embodiments, the disclosure relates to a system comprising devices disclosed herein wherein the device is connected to a lipid membrane comprising a receptor of the ligand. Typically, the receptor is binding the ligand causing an increase in light. In certain embodiments, the lipid membrane is a cell, liposome, micelle, or bilayer sheet.

In certain embodiments, the disclosure relates to methods comprising the steps of: a) exposing any of the devices disclosed herein to a sample suspected of containing a receptor to the ligand and b) detecting changes in the light signal. In certain embodiments, the sample suspected of containing a receptor to the ligand is a cell or bodily fluid obtained from a subject. In certain embodiments, the method further comprises the step of quantifying the light signal. In certain embodiments, the quantifying is automated on a computer. In certain embodiments, method further comprises outputting quantification results. In some embodiments, the method further comprises recording the detected changes on a computer-readable medium through a visual device such as a camera or video recorder.

In certain embodiments, the disclosure relates to methods of determining the effects of a sample compound on a cell or a lipid membrane comprising a) mixing a test compound with a system comprising any of the devices disclosed herein, wherein the device is connected to the lipid membrane comprising a receptor of the ligand; and b) detecting changes in the light signal.

In certain embodiments, devices disclosed herein may be used in microarrays and surface-based assay materials such as those used in methods of measuring molecular forces.

In certain embodiments, devices disclosed herein may be used for screening molecules of pharmacological interest for effect on cellular adhesion via specific receptors, or for effect on the process of endocytosis.

In certain embodiments, devices disclosed herein may be used in a diagnostic kit used to detect the stiffness of cancer cells, metastatic lung, breast, pancreatic cancer cells.

In some embodiments, the device may be attached to a backing. This backing can be any of a number of polymers, biological molecules, or laboratory equipment to which the linker is attached. In some embodiments, the backing may be a microscope slide.

The device can be configured to measure the binding force between the ligand and a receptor. To make this measurement, the device can be immersed in a solution containing receptors that correspond to the ligand. Then, the signal can be examined. In some embodiments, the signal examination can be performed using a microscope. In some embodiments, the signal is examined in an automated fashion.

In some embodiments, the signal examination is quantified. In some embodiments, the quantification is automated.

In some embodiments, the device can be included in a microarray, where a plurality of the cell detectors (either all the same embodiment or different embodiments) can be placed in a plurality of sites in order to examine multiple cell detectors at the same time.

In certain embodiment, the disclosure relates to methods of using the devices disclosed herein comprising the steps: immersing the device in a solution containing biological cells and detecting changes in fluorescence. In certain embodiments the method further comprises the step of quantifying the fluorescence. In some embodiments, the method further comprises outputting quantification results. In some embodiments, the method may further comprise recording the detected changes on a computer-readable medium through a visual device such as a camera or video recorder.

DNA Probes that Store Mechanical Information Reveal Transient Piconewton Forces Applied by T Cells Molecular tension-based fluorescence microscopy (MTFM) was developed to address the challenge of real-time mapping of the pN forces exerted by live cells. MTFM probes are contain a surface-immobilized "spring-like" element that is flanked by a fluorophore and quencher and presents a ligand for receptor recognition. MTFM probes are designed is to maximize fluorophore quenching when the probe is at rest, and to conversely minimize quenching when the probe experiences pN force.

One challenge in MTFM pertains to imaging transient mechanical events. This is because MTFM probes rapidly refold (within μs) upon termination of the mechanical input. Hence long-lived molecular forces or forces mediated by high-copy number receptors have been the focus of MTFM studies. Even single molecule imaging of MTFM probes, which is difficult to implement in live cells, fails to capture rare mechanical events or transient mechanical events with a lifetime below that of the fluorescence acquisition time window (>100 ms).

Wang et al. report thee use of tension gauge tether technology, which employs DNA-duplex probes that are irreversibly denatured at specific thresholds of forces. Science 340(6135):991-994. However, the minimum detectable force threshold is ~12 pN applied for a duration of 2 s; hence, the tension gauge tether approach is not appropriate for detecting weak, or short-lived mechanical events. Thus, there is a need to develop probes to detect infrequent or short-lived mechanical events actively generated by cells.

Disclosed herein is the concept of dynamic mechanical information storage to record and erase molecular force signals (FIG. 1A). To achieve this goal, a stem-loop DNA hairpin that has a defined force-extension relationship was used (real-time closed, FIG. 1A). DNA MTFM probes are highly modular, and the equilibrium force that leads to a 50% probability of hairpin unfolding (real-time open, FIG. 1A), F1/2, can be tuned by adjusting the GC content and length of the stem-loop structure. DNA MTFM probes unfold and rapidly refold in response to molecular forces applied by cell receptors.

Figure 1B:
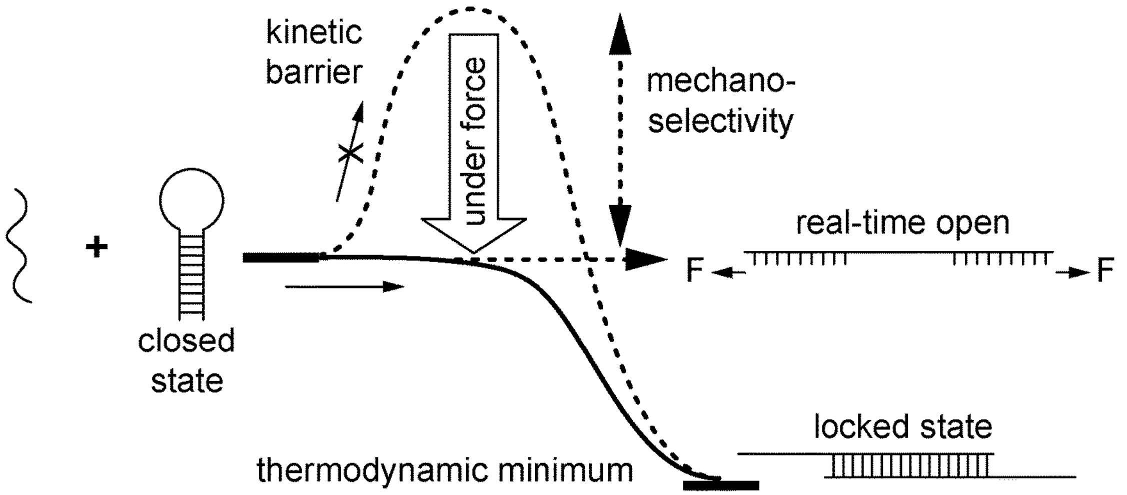
FIG. 1B illustrates an idealized energy diagram showing how mechanical forces dampen the kinetic barrier to locking strand binding, thus affording mechano-selectivity. Images were taken using reflection interference contrast microscopy (RICM), Cy3B, and Atto647N total internal reflection fluorescence (TIRF) of a single OT-1 cell before and after adding the locking strand and after unlocking (toehold mediated displacement).

Storage of mechanical events is mediated by a "locking" oligonucleotide that selectively hybridizes to mechanically unfolded hairpins and prevents refolding (FIG. 1B). Therefore, mechanical unfolding of probes is irreversible upon addition of the locking strand (locked, FIG. 1A). The locking strand can be modified with a fluorophore, Atto647N, to report the accumulation of mechanical events that equal or exceed F1/2. This accumulated mechanical signal can subsequently be erased by an "unlocking" strand that triggers a toehold-mediated strand displacement reaction (FIG. 1A).

Using a mechanical information storage strategy, one is able to perform multiple cycles of storing and erasing of T-cell receptor (TCR) forces and map tension in static and migratory primary CD8+ T cells. This method reveals the mechanical sampling dynamics of TCRs challenged with the antigenic pMHC, along with near-cognate pMHC ligands displaying single amino acid mutations. The results demonstrate that the TCR mechanically samples antigenic pMHCs with forces >4.7 pN, and the frequency as well as area coverage of mechanical sampling is sensitive to single amino acid mutations.

Finally, the locking MTFM probes show that the programmed cell death receptor 1 (PD1), an immune checkpoint inhibitor, transmits pN forces to its ligand in primary T cells, i.e., pN force transmission through the PD1-PDL2 complex, which underscores the power of mechanical information storage in capturing fleeting mechanical events generated by low abundance receptors.

The Selectivity of Lock Strand Binding to Unfolded Hairpins Over Folded Ones

The selectivity of lock strand binding to unfolded hairpins over folded ones was measured by using model surfaces that either presented a folded MTFM probe or an unstructured single stranded DNA sequence. The unstructured sequence included a complementary region to the 17mer, thus providing a model for the opened state of the MTFM hairpin probes. The hybridization of locking strand to the unstructured sequence saturated in seconds. In contrast, lock strand hybridization to the closed hairpin tension probe did not saturate even after 8 h of incubation. Observed rates of binding to a stem-loop hairpin displayed a fast regime representing "kissing" at the loop site, and a slow regime of intermolecular base pairing with the stem. Hybridization yield was also shown to be significantly lowered when targeting a hairpin structure compared to an unstructured sequence.

Assuming pseudo first-order binding kinetics, the data was fitted using one-phase association and a 487-fold difference in binding rates was obtained, thus providing an estimate of the lock binding selectively between mechanically unfolded and folded probes. This analysis ignores the effect of tension on $k_{hyb}$, which is a reasonable assumption given that optical tweezers measurements show that $k_{hyb}$ is not impaired when the load is less than 20 pN. Interestingly, weak forces applied to a ssDNA slightly promote hybridization, as tension helps with aligning the strand at initial encounter. Conversely, mechanical stretching of DNA with large values of tension is expected to hinder hybridization. This is because forming the B-form duplex becomes less energetically favorable. Indeed, when $F \approx 40$ pN for a 24mer, this created a barrier to hybridization. However, quantifying TCR-pMHC N4 forces showed that TCR force values fail to unfold DNA hairpins with a $F_{1/2}=19$ pN. Given that TCR forces are below 19 pN, estimates of mechano-selectivity are justified here.

Another consideration is the role of the lock strand concentration in capturing transient unfolding events. If the rate of $k_{hyb}$ is slow relative to the lifetime of the mechanical event, then mechanical information storage will fail. At high concentration of lock strand, the vast majority of hairpin unfolding events will lead to lock binding and mechanical information storage. Quantitative analysis of the kinetics of tension signal accumulation as a function of lock strand concentration likely provides a direct measurement of force lifetimes (τforce).

EXAMPLES

Transformation of Oligonucleotide Complexes

Oligonucleotides were screened to identify appropriate candidates for mechanically-selective hybridization. Ideally, the locking oligonucleotide must rapidly bind to the unfolded hairpin and also display thermodynamic stability such that it remains bound to the probe for the duration of the experiment. Since the binding target is a stem-loop hairpin, these two properties are at odds, as the most thermodynamically stable locking strand is a full complement, which will also form a hairpin itself, thus hindering the rate of locking. Conversely, shorter locking strands that lack the full stem enhance the rate of locking but reduce thermodynamic stability.

Figure 7B:
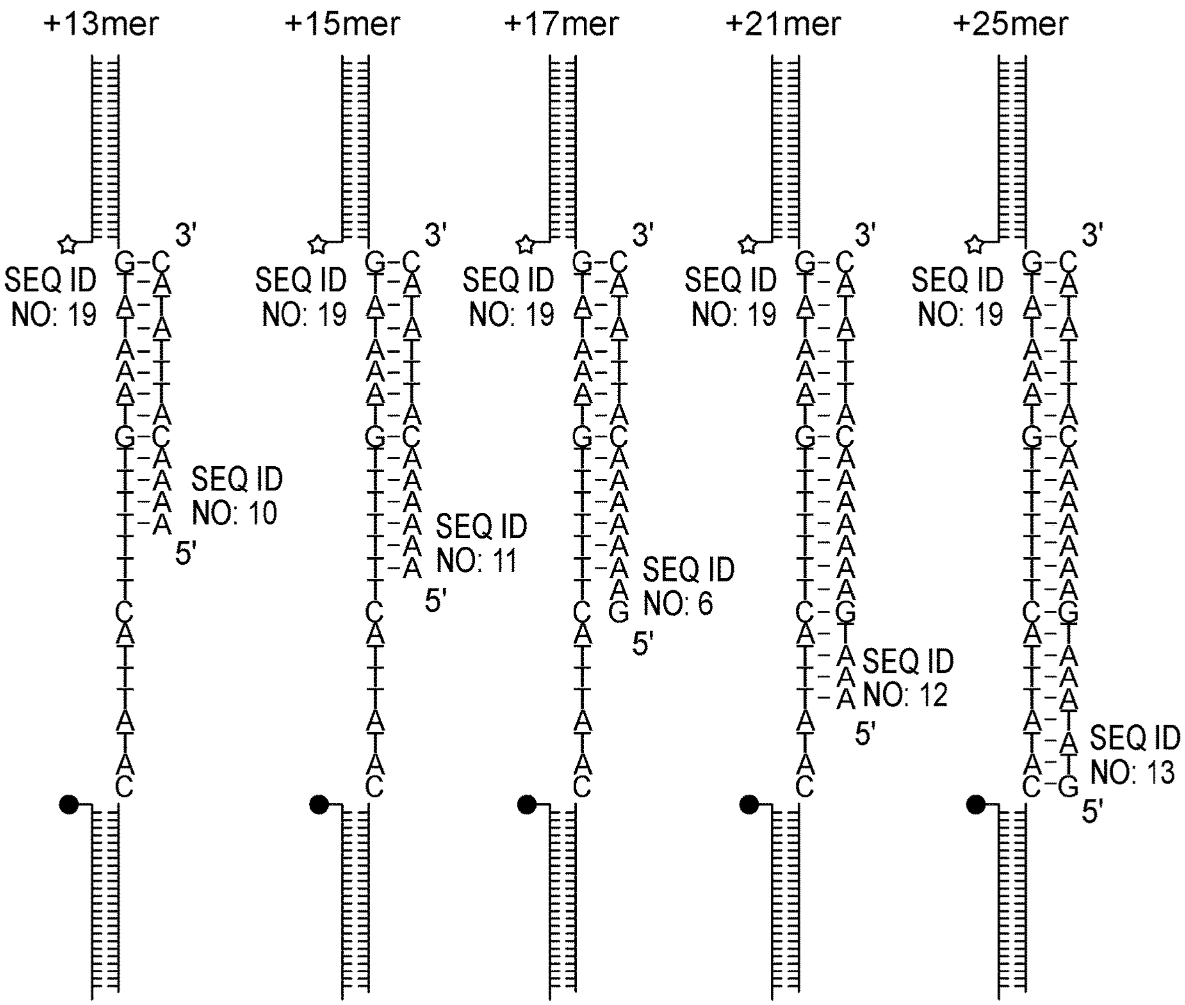
FIG. 7B illustrates the duplex alignment after hybridization. The stem-loop region is indicated by SEQ ID NO: 19, locking oligonucleotides by (SEQ ID NOs: 10-13) and the 17 mer lock (SEQ ID NO: 6).
Figure 7C:
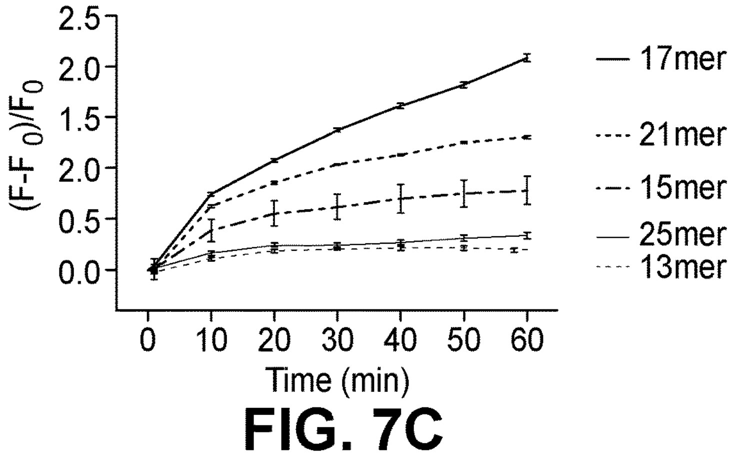
FIG. 7C shows data indicating the 17mer displayed optimal hybridization to the MTFM probes. Fluorescence measurements of in-situ hybridization kinetics between the immobilized MTFM probes and the locking oligonucleotides at 200 nM. Locking oligonucleotides were added to surfaces presenting the MTFM tension probes at room temperature and allowed to bind to the hairpin for >1 h. Hybridization was monitored by the increase in fluorescence due to hairpin opening.
Figure 9:
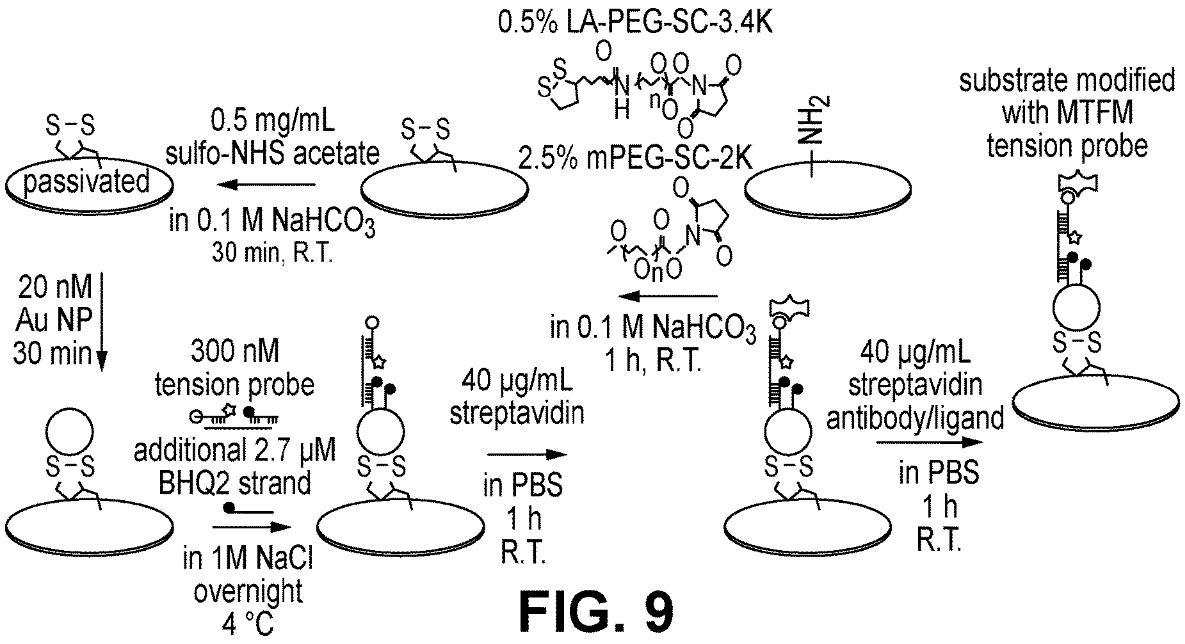
FIG. 9 illustrates preparation of certain surfaces with MTFM probes.

Based on these criteria, five different locking oligonucleotides were designed that ranged in length from 25mer to 13mer to screen (FIG. 7A). Gold nanoparticle MTFM tension probe surfaces were prepared (FIG. 9). Atomic force microscopy and fluorescence microscopy showed that the tension probe substrates were uniform and displayed an average of 1000 plus/minus 89 gold nanoparticles/μm$^2$, with approximately 4.4 DNA tension probes per gold particle. The locking oligonucleotides were tested. The 17mer has the most desirable properties (FIG. 7C). To estimate mechanoselectivity, the differential binding of locking strand to MTFM probe at rest to that of an unstructured sequence (mimicking opened state of MTFM probe) were compared. A difference greater than two orders of magnitude was found.

Figure 8A:
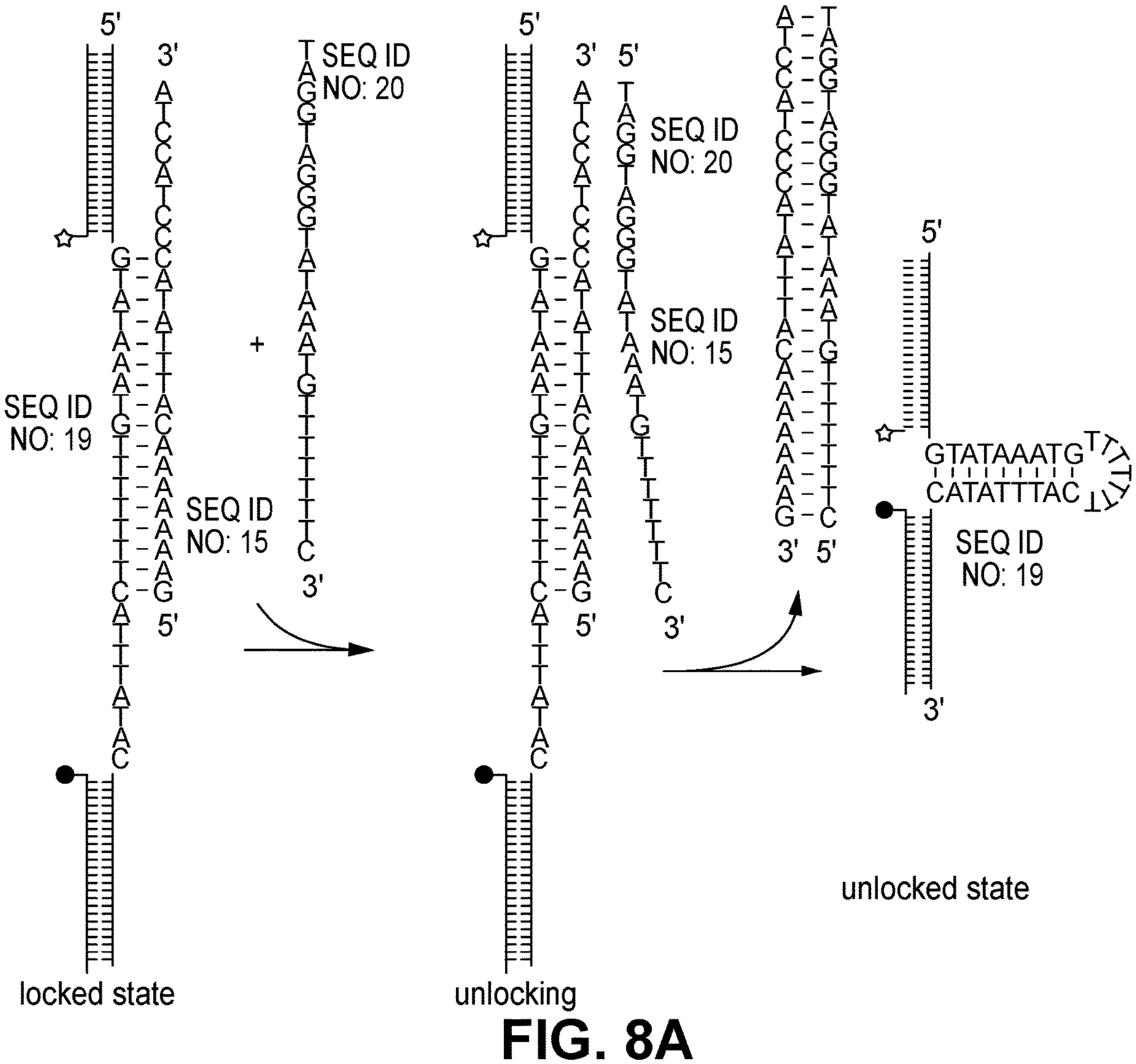
FIG. 8A illustrates toehold-mediated displacement reaction (unlocking). The MTFM tension probe (SEQ ID NO: 19) was annealed with the locking strand (17mer) (SEQ ID NO: 15) before immobilization onto the surface. The unlocking strand (SEQ ID NO: 20) is added.
Figure 8B:
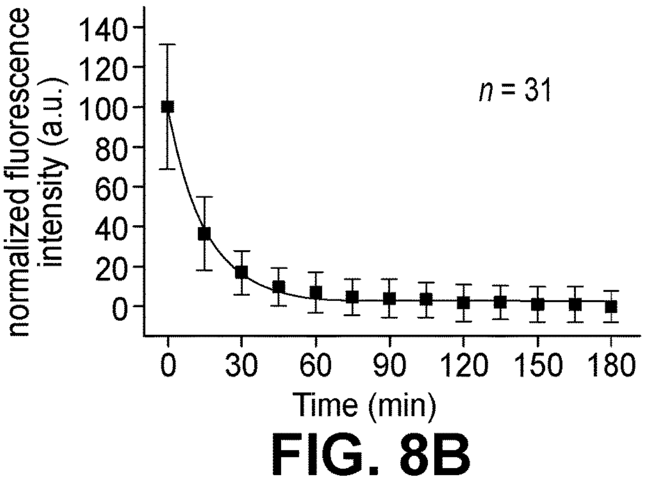
FIG. 8B shows data where naïve OT-1 cells were allowed to produce tension against antiCD3ε on tension probe substrates. The mechanically opened probes were locked with 200 nM locking strand over 10 min. After rinsing away excess locking strand, the unlocking strand was added at a final concentration of 200 nM, and the tension signal for the same cells was measured as a function of time.

For unlocking experiments, an 8 nt toehold was engineered with 50% GC content at the 3' end of the locking strand. The addition of unlocking strand triggered a rapid toehold-mediated strand displacement reaction that released locking strands from the DNA probes, resetting the probes to the real-time closed state (FIG. 8A and 8B).

Locking/Unlocking in Live Cells

To test locking/unlocking the oligonucleotide complexes in live cells, naïve OT-1 T cells were allowed to adhere and spread on MTFM probe surfaces presenting antiCD3ε antibodies. Cells generated tension signal as the TCR engaged the antibody and transmitted forces to the probes. Subsequently, the Atto647N-tagged locking strand was added for 10 min, washed, and the same T cells were imaged, confirming binding. Importantly, the Cy3B hairpin signal increased after the locking strand was introduced, indicating that the locking strand lead to the accumulation of opened hairpins. Significant co-localization between the Cy3B (hairpin opening) and the Atto647N (locking strand) signals was found, as evident from linescan analysis and the Pearson's correlation coefficient of 0.72±0.096 (n=20 cells). The excess locking strand was rinsed away before re-imaging. "Erasing" the stored cellular mechanical information was tested. This process was triggered by adding 200 nM unlocking strand to the sample for 2-3 min and confirmed by imaging the same group of T cells. The unlocking process was rapid and reached completion within 60 s. Control experiments using tension probes with a scrambled stem-loop confirmed the specificity of locking real-time tension. Time-lapse videos confirmed the unlocking of stored information was due to toehold-mediated strand displacement rather than photobleaching and was sequence specific. Control experiments using latrunculin B (5 μM, 15 min), a cytoskeletal inhibitor, confirmed that the locked tension was maintained even when receptor forces were minimized.

Figure 2A:
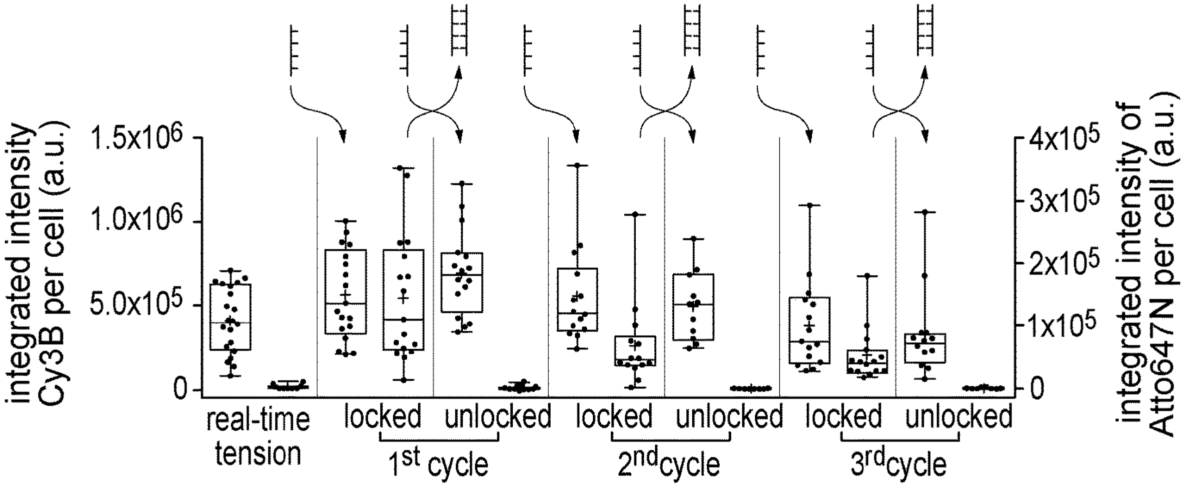
FIG. 2A shows a plot displaying the Cy3B (hairpin opening) and Atto647N (locking strand) integrated intensity per cell for a population of cells that underwent three cycles of locking and unlocking. RICM, Cy3B (hairpin opening), and Atto647N (locking strand) images of a single OT-1 CD8+ T cell underwent three rounds of mechanical information storage and erasing. Locking was driven with a 200 nM solution of oligo for a duration of 10 min, while unlocking was triggered using 100 nM unlocking probe for a duration of 3 min. The Atto647N signal drops to background levels upon addition of the unlocking strand. The bars display the contrasts used to display each set of fluorescence images.

One advantage of this strategy is the ability to arbitrarily toggle between the locked and unlocked states of the probe, thus selecting different time windows for integrating the force signal. Accordingly, multiple rounds of mechanical information storage and erasing were performed. TCR-antiCD3ε forces were first imaged, and 200 nM locking strand was subsequently added to accumulate tension signal for 10 min. Excess locking strand was then washed away, and stored tension images were acquired. The stored tension signal was then erased with 100 nM unlocking strand for 3 min. This procedure was repeated for two additional cycles, and the hairpin opening and locking strand signal for the same naïve OT-1 cell was imaged. Statistically significant changes were observed in integrated Atto647N fluorescence intensity upon addition of locking or unlocking strand (FIG. 2A). The hairpin opening signal varied during three cycles. This reflects the mechanosensitive nature of the TCR which experiences forces during addition and washing of the oligonucleotide probes, and also represents some T cell fatigue over the duration of the experiment (>1 h). As the maximum number of cycles depends on the duration of the imaging experiment, cell exhaustion could be avoided by using microfluidics in future applications.

Mapping Receptor Forces Produced by Migratory T Cells

Figure 2B:
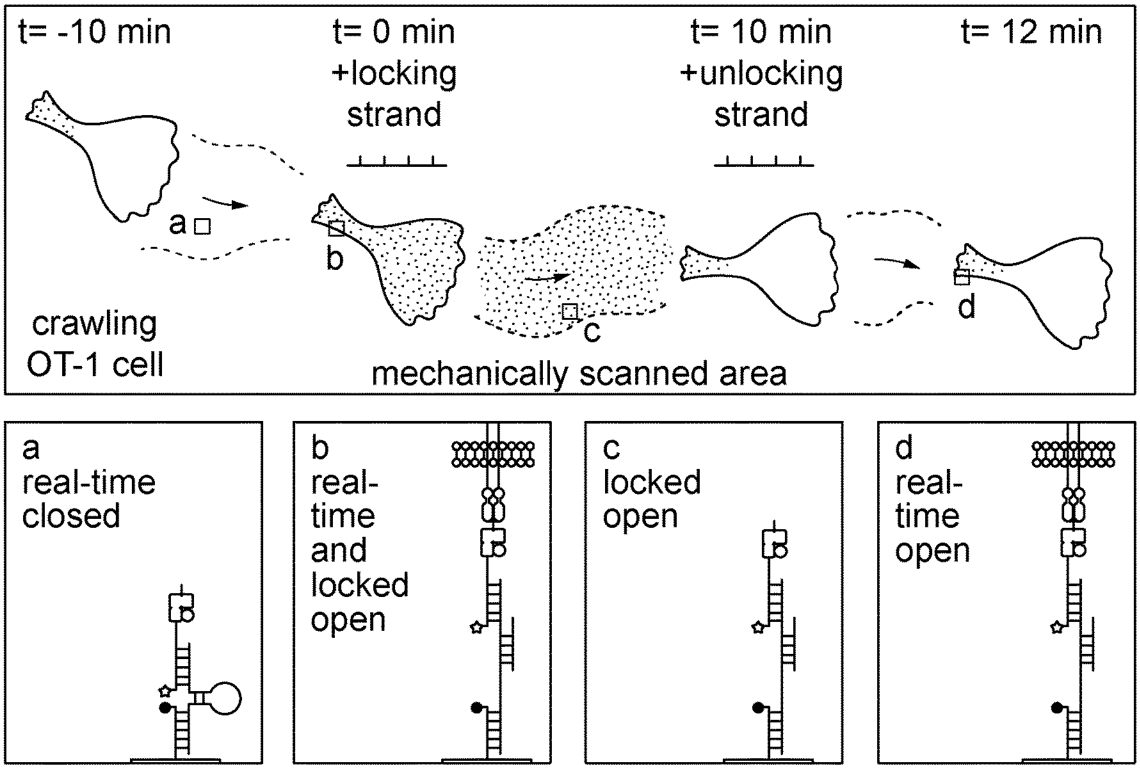
FIG. 2B shows a schematic on how mechanical information storage was used to map mechanical sampling/scanning of pMHC antigen during cell migration using RICM and tension images of a single T cell crawling on an ICAM-1/pMHC N4 surface.

The ability to map TCR forces produced by a migratory T cell were investigated (FIG. 2B). To trigger the migration, surfaces were engineered presenting ICAM-1, the ligand of a T cell adhesion receptor, lymphocyte function associated antigen 1 (LFA-1), along with the antigenic N4 pMHC (peptide: SIINFEKL (SEQ ID NO: 22), which is a commonly studied OT-1 TCR antigen derived from chicken ovalbumin. LFA-1 is crucial in T cell activation, adhesion and crawling. Therefore, the co-presentation of these two ligands triggers a highly migratory phenotype of OT-1 cells. The TCR tension was primarily located at the trailing edge of the cells and was highly transient, dynamically following the cellular trajectory along the substrate. Motile T cells show a distinct TCR force map compared to static cells exclusively stimulated with N4 pMHC; the latter formed a ring-like tension pattern that evolved to distribute across the cell-substrate contact area. Upon addition of the locking strand, the TCR tension signal was enhanced and also extended across the T cell track, revealing the spatial distribution of pMHC ligands scanned with F >4.7 pN over 10 min. Interestingly, these images show that the T cell mechanically scanned a significant fraction of antigen (81 plus/minus 28% over its initial contact area, n=10 cells) within a 10 min migration time window. Thus, the dynamic T cell synapse (kinapse) represents a zone of TCR mechanosensing. Upon addition of the unlocking strand, probes "reset" back to the real-time state, and exclusively showed tension at the trailing edge of the cell. Taken together, these experiments show the utility of the locking/unlocking strategy to visualize the molecular forces associated with static and migratory T cells across different time scales.

Mechano-locking enhances TCR-pMHC tension signals by accumulating pulling events that are >4.7 pN. The degree of enhancement and dynamics were evaluated. OT-1 T cells were allowed to engage real-time tension probes and then incubated with unlabeled locking strand (200 nM). The unlabeled locking strand was beneficial here because it eliminated bleed-through from the Atto647N tag. Additionally, avoiding the rinsing steps accelerates the experiments and reduces perturbation of cells.

Discriminating Between Single Amino Acid Ligand Mutants

Figure 3A:
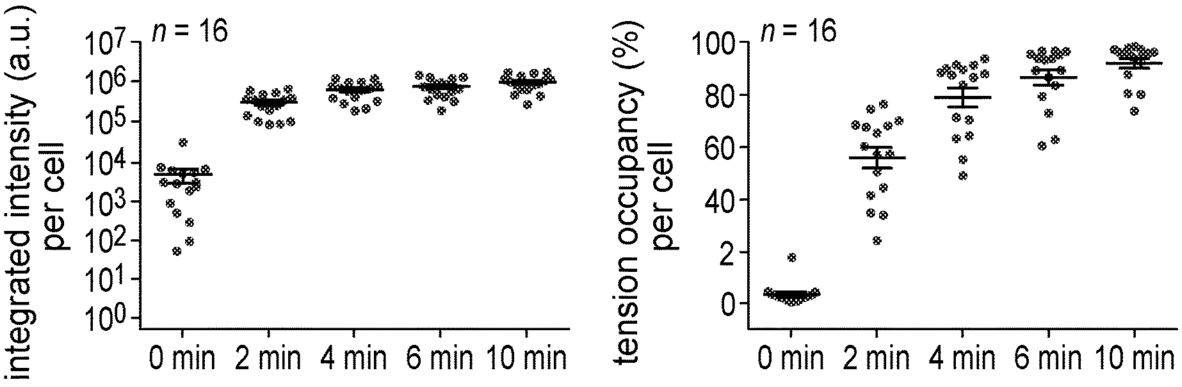
FIG. 3A shows plots of integrated tension signal and tension occupancy of individual cells as a function of time (n=16 cells from the same animal).

A time course for TCR-N4 pMHC tension signal accumulation for three cells upon addition of the locking strand was imaged. Analysis of kinetics for n=16 cells showed that the signal approached saturation by t=10 min (FIG. 3A). Notably, the enhancement of the integrated N4 tension signal per cell was approximately 189-fold in this experiment. Tension occupancy, which is the fraction of the cell contact area showing tension signal, reached 91% in 10 min. The tension occupancy is an indication of the area that is mechanically scanned by the TCR with F >4.7 pN in search for antigen.

T cells mechanically sample their cognate and near cognate ligands over time. The TCR-pMHC interaction is highly specific, allowing T cells to discriminate between single amino acid mutants of the cognate pMHC despite their similar μM-range 3D affinity. Single molecule force spectroscopy measurements suggest that the stability of the TCR-pMHC complex at differing levels of mechanical strain provides a mechanism to enhance antigen discrimination. A panel of well-characterized altered peptide ligands, as well as antiCD3ε, against OT-1 cells was tested. TCR tension maps of naïve OT-1 cells challenged with the cognate N4 pMHC and single amino acid mutants of the 4th position of SIIXFEKL (SEQ ID NO: 23), where X=Q, V, and G. In the real-time state, cells produced the greatest tension signal with antiCD3ε, followed by N4, with the mutant pMHC antigens producing weak or non-detectable tension signal. This result is consistent with work with V4 and also with the reported bond lifetimes for mutant ligands. For example, independent of CD8, TCR-pMHC N4 binding displays catch-bond behavior, with an average bond lifetime of 100 ms at zero force and 800 ms at 10 pN. However, the TCR exhibits slip-bond behavior with the mutant pMHC G4 (SIIGFEKL (SEQ ID NO: 24)), displaying an average bond lifetime of 300 ms at zero force and <100 ms at 10 pN. Such short-lived mechanical events are difficult to visualize with real-time probe imaged with conventional epifluorescence microscopy. Upon addition of the locking strand, the integrated tension signal was significantly enhanced in all the tested antigens due to the accumulation of mechanical events over a time window of 10 min. Though mechanical events mediated between TCRs and weak antigens are transient and previously undetectable, the addition of the locking strand amplified the tension signal and rendered it distinguishable. The less potent pMHC Q4 produced a ring-pattern that could be observed after locking, though it was much less pronounced compared to the N4 antigen. With pMHC V4 and G4, the observed tension did not show the typical ring-pattern and was more disorganized. The mutant antigens showed significantly weaker integrated tension and tension occupancy, which can be attributed, in part, to TCR-pMHC bond failure as well as the lack of T cell triggering.

Figure 3B:
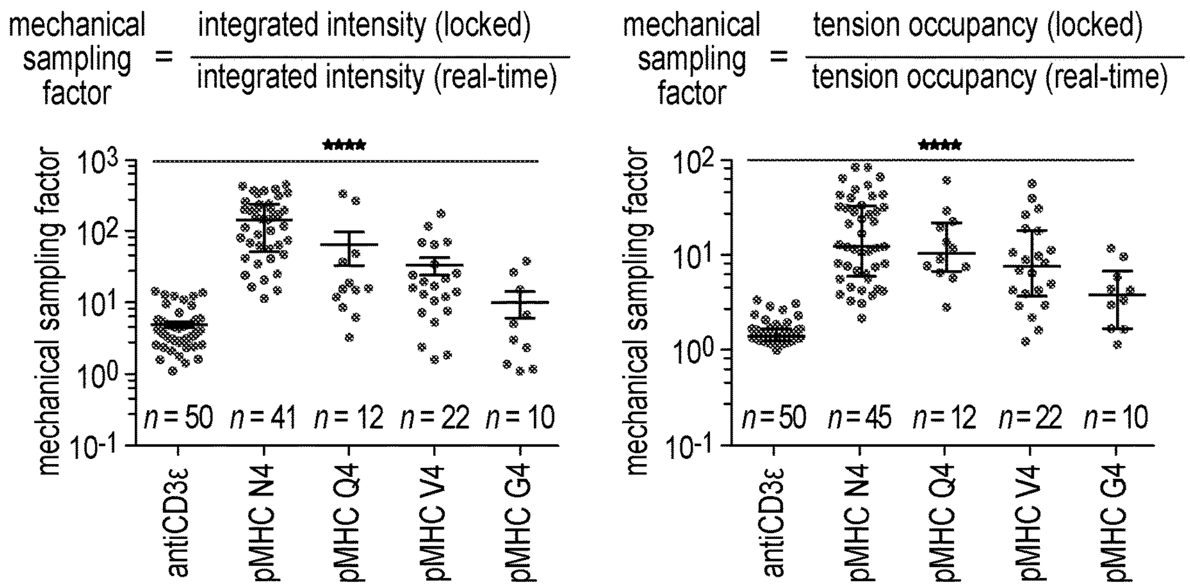
FIG. 3B shows data where single cells were imaged using probes in the real-time and locked state when presented with antiCD3epsilon, pMHC N4, Q4, V4, and G4.
Figure 3C:
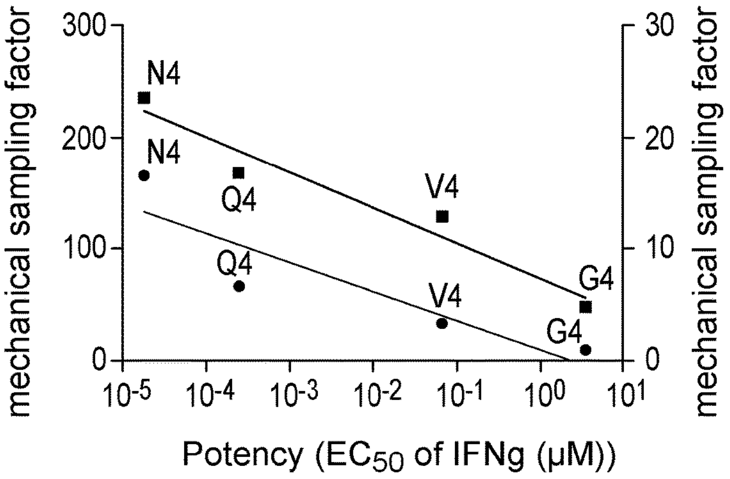
FIG. 3C show a correlation between the mechanical sampling and scanning factor and the potency of the ligand based on known $EC_{50}$ values.
Figure 3D:
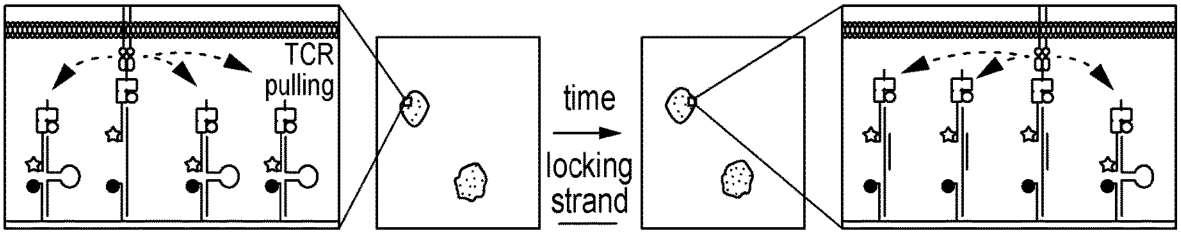
FIG. 3D is a schematic illustrating the concept of mechanical sampling and scanning.

The signal accumulation levels differed when cells were presented with antibody, cognate pMHC, and altered peptide ligands. To quantify these differences on a per cell basis, two parameters were defined: the mechanical sampling factor, which is the fold enhancement in integrated tension signal; and the mechanical scanning factor, which reflects the fold increase in tension occupancy (FIG. 3B). These factors reflect the frequency of TCR binding to antigens, applying F >4.7 pN, dissociating, and then sampling new ligands (FIG. 3B). Interestingly, the integrated tension signal and the tension occupancy varied significantly when the OT-1 cells were exposed to different antigens. Plots in FIG. 3B show the mechanical sampling and mechanical scanning factors for different TCR ligands averaged from n >10 cells per group.

Surprisingly, the average mechanical sampling factor was only 5 plus/minus 0.5 for antiCD3ε, whereas for N4 it was 165 plus/minus 21, followed by 66 plus/minus 32, 33 plus/minus 9, and 10 plus/minus 4 for the Q4, V4, and G4 antigens, respectively (FIG. 3B). Though the real-time tension with antiCD3ε was the greatest among all tested ligands, it failed to accumulate as fast as N4, implying less frequent mechanical sampling by the TCRs, which is likely partially due to the slow $k_{off}$ of the antibody. The difference in 2D kinetics of TCR-ligand interaction is likely an important contributor to the significant difference in mechanical sampling factor across the panel of ligands. For example, independent of CD8 engagement, the TCR-pMHC N4 interaction has an effective 2D on-rate $A_c k_{on}$=1.7 plus/minus $10^{-3}$ $\mu m4s^{-1}$ at 25 ° C. This rapid on-rate enables T cells to search for and sample antigens at high speed, and quickly accumulate sufficient antigen stimulation for further signaling. In contrast, for less potent pMHC G4, $A_c k_{on}$=4.7 plus/minus $10^{-5}$ $\mu m4s^{-1}$ which leads to slower binding, and thus contributes to a smaller mechanical sampling factor. There has been long standing speculation that the rapid kinetics of TCR-antigen binding provides an advantage in terms of maximizing sampling of antigen, and these results confirm this notion through the mechanical sampling factor for N4. The mechanical scanning factor, which is a measure of the increase in tension occupancy, and is related to cytoskeleton coordination of TCRs, showed similar trends.

Mechanotransduction of the Programmed Cell Death Receptor 1 (PD1).

PD1 is a coinhibitory receptor that downregulates T cell activation when it encounters its ligands, programmed cell death ligand 1 (PDL1) and/or ligand 2 (PDL2). To test the potential of mechanical information storage to detect forces generated by low abundance receptors, PD1 was investigated. PD1 density is low in naïve OT-1 CD8+ cells, with 0.2 molecules per $\mu m^2$ (about 24 copies per cell), and 6.8 molecules per $\mu m^2$ (about 671 copies per cell) in antibody-stimulated activated cells.

Figure 4A:
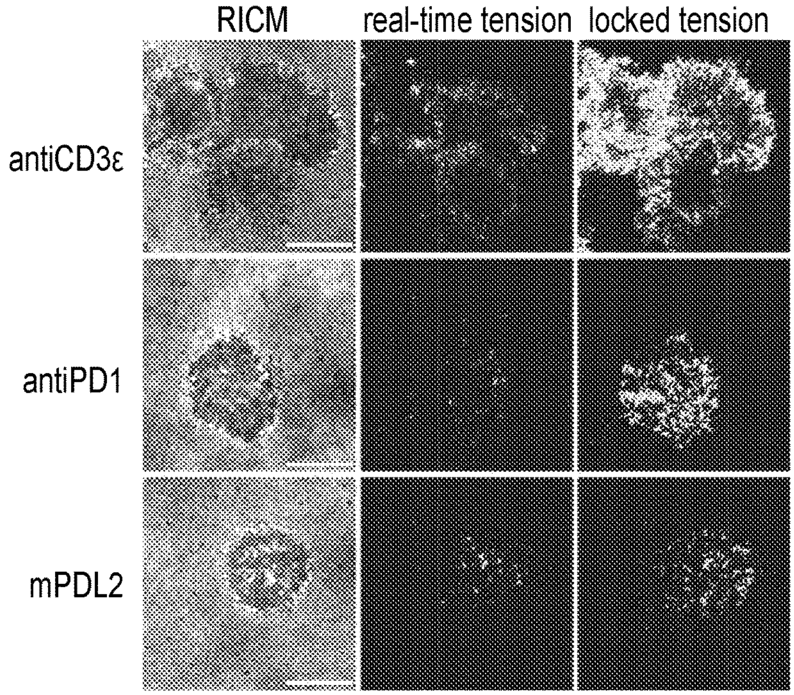
FIG. 4A are images of representative RICM and tension images of activated OT-1 cells on antiCD3ε, antiPD1, and mPDL2-functionalized tension probes in the real-time and locked state (10 min duration).
Figure 4B:
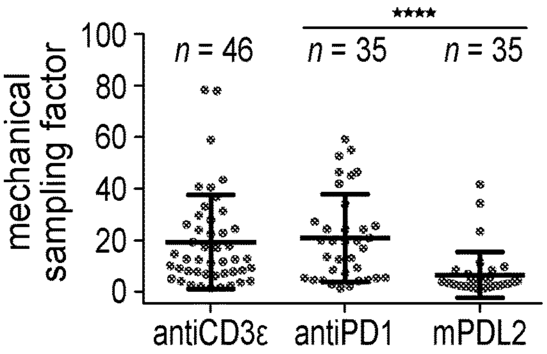
FIG. 4B is a plot of mechanical sampling factor for antiCD3ε, antiPD1, and mPDL2 in activated OT-1 cells derived from RICM and tension images of activated OT-1 cells on antiCD3ε, antiPD1, and mPDL2-functionalized tension probes in the real-time and locked state (10 min duration).
Figure 4C:
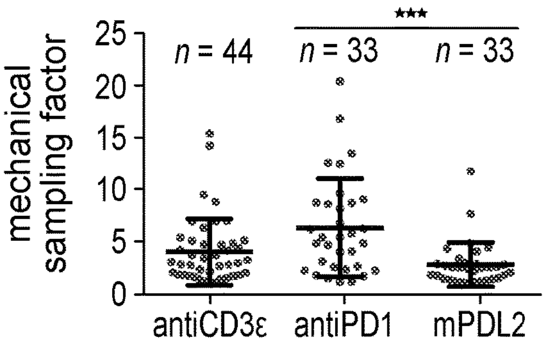
FIG. 4C is a plot of mechanical scanning factor.
Figure 5A:
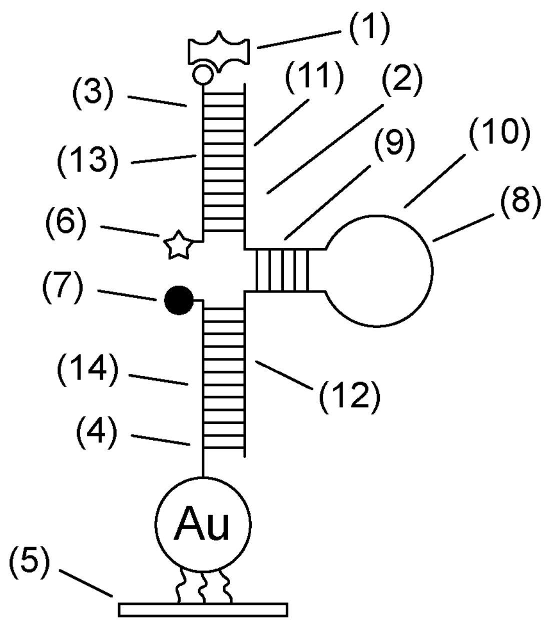
FIG. 5A illustrates a device comprising: i) a ligand (1); ii) a nucleic acid complex linker (2) having a first end (3) and a second end (4), wherein the nucleic acid complex linker (2) is linked to the ligand (1) at the first end (3); iii) a surface (5) connected to the nucleic acid complex linker (2) at the second end (4); iv) a first fluorescent molecule (6) conjugated to the nucleic acid complex linker (2) wherein the fluorescent molecule (6) is configured to move its position relative to the surface (5) or a quencher (7) when the ligand (1) moves; and v) a quencher (7) is conjugated to the nucleic acid complex linker (2) wherein the quencher (7) is fixed to the surface (5) when the ligand (1) moves, wherein the nucleic acid complex linker (2) comprises a hairpin motif (8) comprising a double stranded stem segment (9), a single stranded loop segment (10), a first end tail segment (11), and a second end tail segment (12); wherein the first end tail segment (11) hybridizes with a first tail segment complement (13) conjugated to the first fluorescent molecule (6); wherein the second tail segment (12) hybridizes with a second tail segment complement (14) conjugated to the quencher (7); wherein the quencher (7) and the first fluorescent molecule (6) are configured to quench when the nucleic acid complex linker (2) is in the form of a hairpin motif (8) and the first end tail segment (11) hybridizes with the first tail segment complement (13) and when the second tail segment (12) hybridizes with the second tail segment complement (14). In this configuration the ligand (1) is conjugated to the first tail segment complement (13) and the surface (5) is conjugated second tail segment complement (14).
Figure 5B:
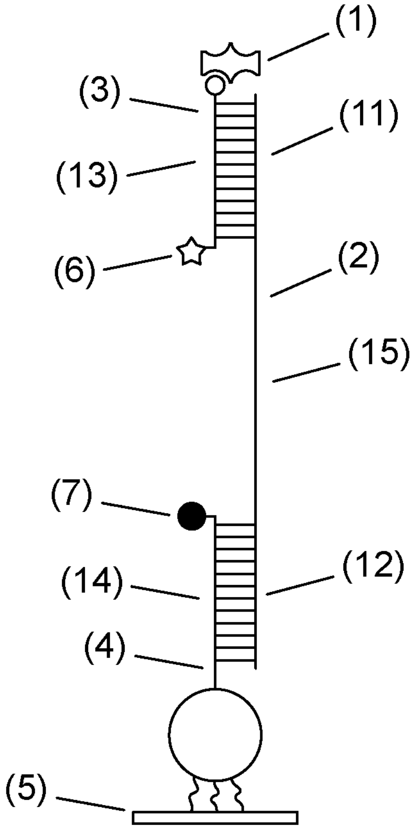
FIG. 5B illustrates a device comprising: i) a ligand (1); ii) a nucleic acid complex linker (2) having a first end (3) and a second end (4), wherein the nucleic acid complex linker (2) is linked to the ligand (1) at the first end (3); iii) a surface (5) connected to the nucleic acid complex linker (2) at the second end (4); iv) a first fluorescent molecule (6) conjugated to the nucleic acid complex linker (2) wherein the fluorescent molecule (6) is configured to move its position relative to the surface (5) or a quencher (7) when the ligand (1) moves; and v) a quencher (7) conjugated to the nucleic acid complex linker (2) wherein the quencher (7) is fixed to the surface (5) when the ligand (1) moves, wherein the nucleic acid complex linker (2) comprises a single stranded motif (15), a first end tail segment (11), and a second end tail segment (12); wherein the first end tail segment (11) hybridizes with a first tail segment complement (13) conjugated to the first fluorescent molecule (6); wherein the second tail segment (12) hybridizes with a second tail segment complement (14) conjugated to the quencher (7); wherein the quencher (7) and the first fluorescent molecule (6) are not configured to quench when the nucleic acid complex linker (2) is in the form of a single stranded motif (15) and the first end tail segment (11) hybridizes with the first tail segment complement (13) and when the second tail segment hybridizes (12) with the second tail segment complement (14).
Figure 5C:
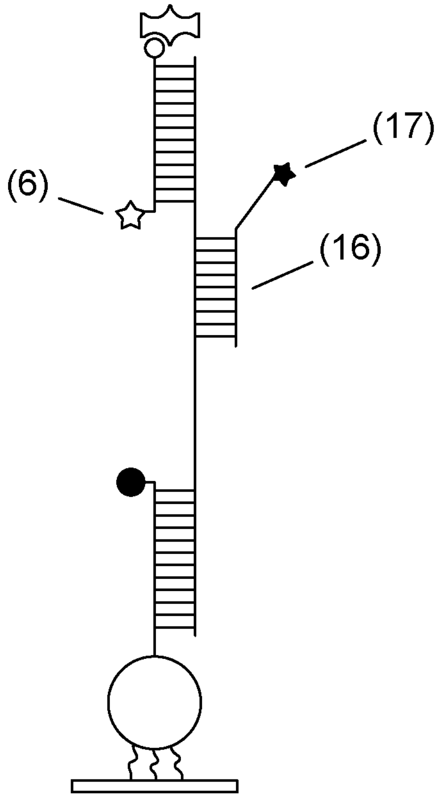
FIG. 5C illustrates the device of FIG. 1B further comprising a toehold oligonucleotide (16) conjugated to a second fluorescent molecule (17) wherein the first fluorescent molecule (6) and second fluorescent molecule (17) have different excitation maximums and/or emission maximums. When the nucleic acid complex folds into a stem loop configuration, this configuration puts the fluorophore and quencher near each other. However, addition of the toehold oligonucleotide (16) for binding to the single stranded form locks the expanded form preventing the formation of the hairpin motif/ stem loop configuration.
Figure 5D:
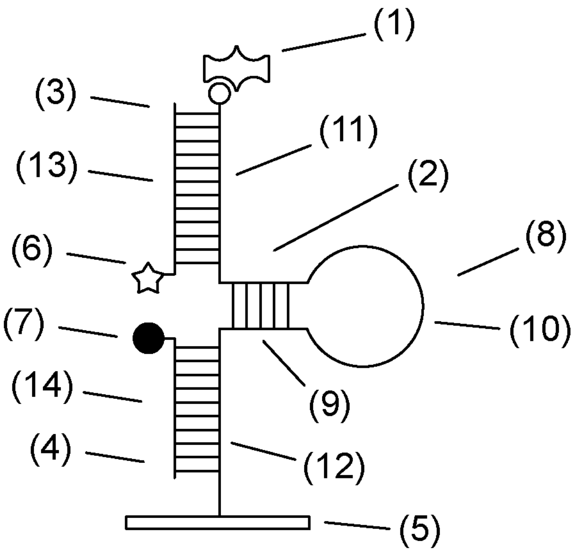
FIG. 5D illustrates a device configure to use the second tail segment (12) to anchor to the surface (5) and the first tail segment (11) to display the ligand (1). In this design, the device comprises: i) a ligand (1); ii) a nucleic acid complex linker (2) having a first end (3) and a second end (4), wherein the nucleic acid complex linker (2) is linked to the ligand (1) at the first end (3); iii) a surface (5) connected to the nucleic acid complex linker (2) at the second end (4); iv) a first fluorescent molecule (6) conjugated to the nucleic acid complex linker (2) wherein the fluorescent molecule (6) is configured to move its position relative to a quencher (7) when the ligand (1) moves; and v) a quencher (7) is conjugated to the nucleic acid complex linker (2), wherein the nucleic acid complex linker (2) comprises a hairpin motif (8) comprising a double stranded stem segment (9), a single stranded loop segment (10), a first end tail segment (11), and a second end tail segment (12); wherein the first end tail segment (11) hybridizes with a first tail segment complement (13) conjugated to the first fluorescent molecule (6); wherein the second tail segment (12) hybridizes with a second tail segment complement (14) conjugated to the quencher (7); wherein the quencher (7) and the first fluorescent molecule (6) are configured to quench when the nucleic acid complex linker (2) is in the form of a hairpin motif (8) and the first end tail segment (11) hybridizes with the first tail segment complement (13) and when the second tail segment (12) hybridizes with the second tail segment complement (14). In this configuration the ligand (1) is conjugated to the first tail segment (11) and the surface (5) is conjugated second tail segment complement (12).
Figure 5E:
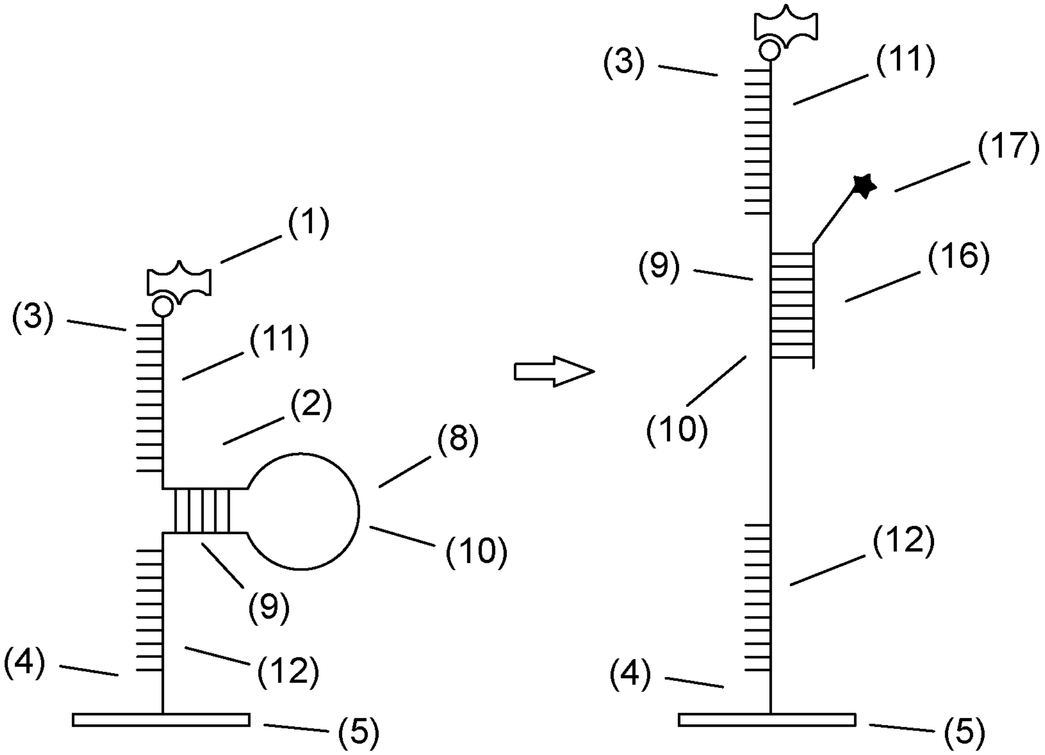
FIG. 5E illustrates a system comprising: a) a device comprising: i) a ligand (1); ii) a nucleic acid complex linker (2) having a first end (3) and a second end (4), wherein the nucleic acid complex linker (2) is linked to the ligand (1) at the first end (3); iii) a surface (5) connected to the nucleic acid complex linker (2) at the second end (4); wherein the nucleic acid complex linker (2) comprises a hairpin motif (8) comprising a double stranded stem segment (9), a single stranded loop segment (10), a first end tail segment (11), and a second end tail segment (13); and b) a locking oligonucleotide (16) that hybridizes with the double stranded stem segment (9) and the single stranded loop segment (10) when a receptor binds the ligand (1) and unravels the hairpin motif (8) providing an extended form derived from a single stranded motif. In certain embodiments, the locking oligonucleotide (16) comprises a label such as a fluorescent molecule (17).
Figure 5F:
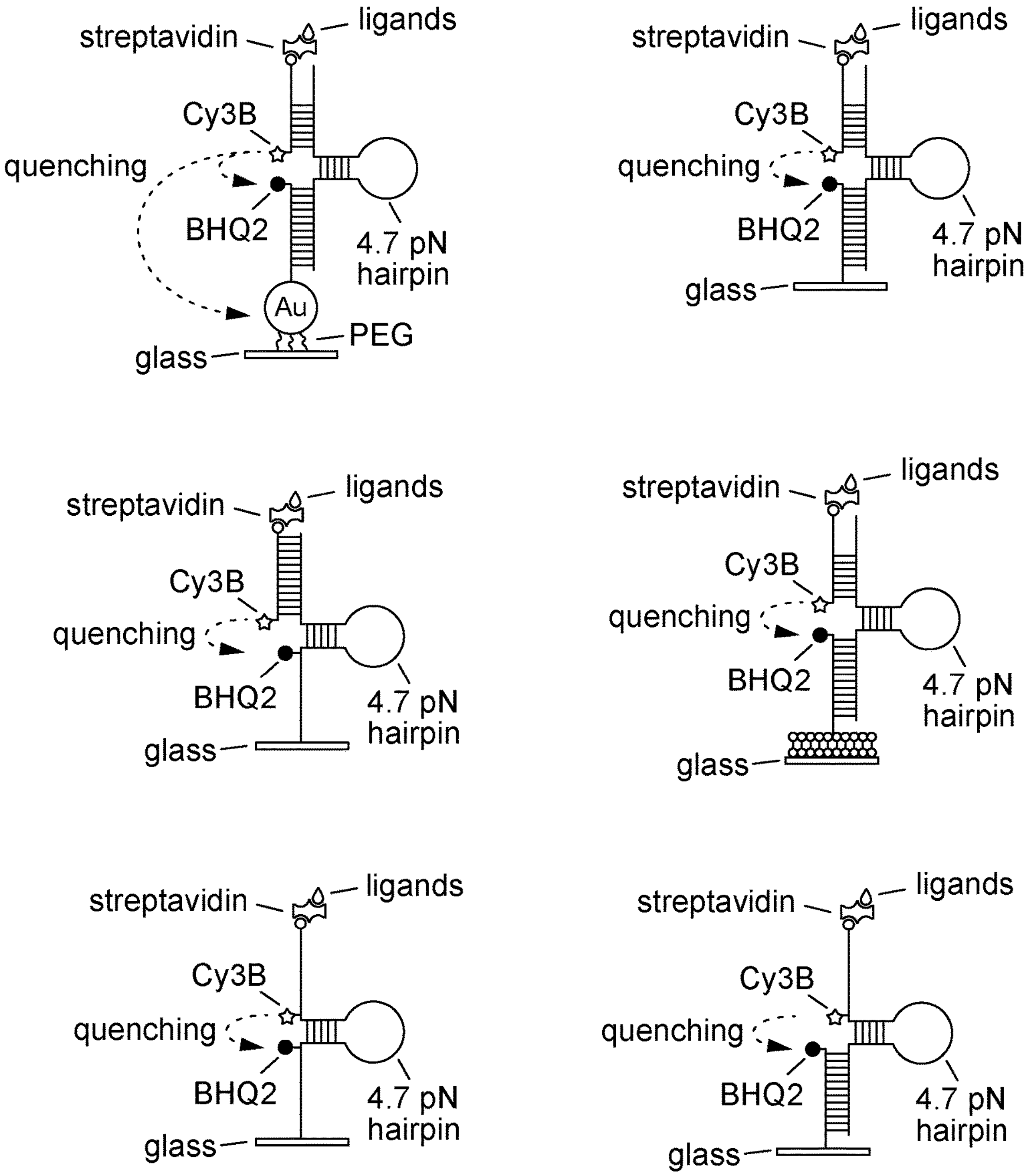
FIG. 5F illustrates additional embodiments of the disclosure. Exemplified are examples wherein biotin is on the terminal end of a nucleic acid complex linker. A ligand is also modified with biotin. Streptavidin is used to conjugate the ligand to the nucleic acid complex linker. The first and second tail end segments may optionally be single or double stranded. In certain embodiments, the first or second ends may be conjugated to the surface that is particle further conjugated to a surface or fixed to a lipid bilayer by the addition of a steroid or lipid to the second end, or directly fixed to a glass surface by silanes or siloxane coupling agents.

Hence, naïve OT-1 cells were activated using the N4 peptide for 48 h, and the activated cells were imaged on tension probes presenting either antiPD1 antibody or murine PDL2. TCR-antiCD3ε forces were also quantified as a positive control. Without the locking strand, the PD1-antiPD1 and PD1-mPDL2 tension was very weak or non-distinguishable from noise. However, the PD1 tension signal was enhanced upon addition of the locking strand (1 μM, introduced 30 min after cell plating) (locked, FIG. 4A). In contrast to TCR forces, PD1-mPDL2 tension was less abundant and more punctate and did not display a typical ring-pattern characteristic for TCR ligands. The integrated tension intensity and tension occupancy were quantified before and after incubation with the locking strand. Both parameters were weaker for the mPDL2 ligand compared to the PD1 antibody, likely reflective of their relative affinities. Even upon addition of the locking strand, there was modest signal enhancement compared to that of the TCR antigens. Employing similar parameters, the mechanical sampling factor was 6.4 plus/minus 1.5 for mPDL2 and 20.8 plus/minus 2.9 for antiPD1 (FIG. 4B). The mechanical scanning factor was 2.9 plus/minus 0.4 for mPDL2 and 6.4 plus/minus 0.8 for antiPD1 (FIG. 4C). These values imply that PD1 forces were less dynamic when T cells were stimulated with mPDL2 compared to antiPD1. It is not clear how the cytoskeleton coordinates the mechanical sampling and scanning features of PD1, but given that PD1-PDL2 binding mediates dampening of T cell activity and adhesion, it is plausible that this difference reflects differential T cell activation upon stimulation with PDL2 versus antiPD1. Taken together, the mechanical information storage approach shows that PD1 transmits F >4.7 pN to its ligand upon surface engagement.

Figure 10:
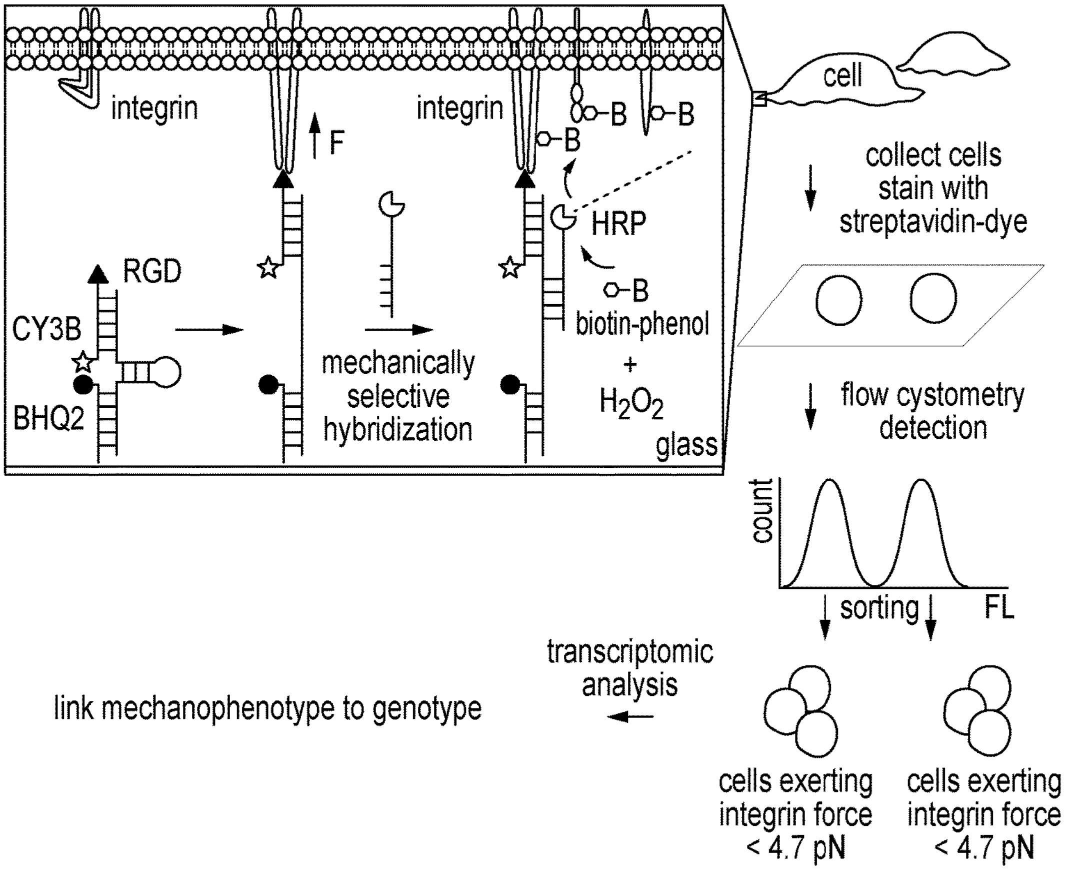
FIG. 10 illustrates mechanophenotyping cells with HRP modified locking strand.
Figure 11:
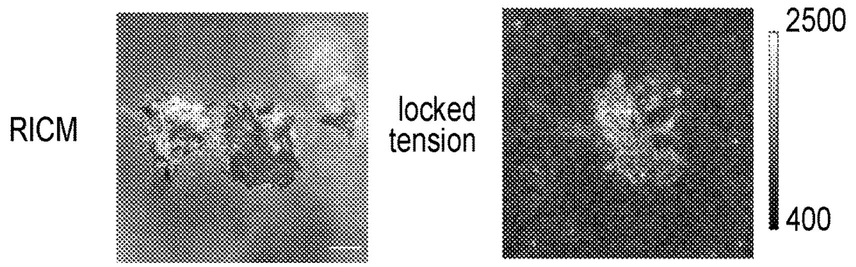
FIG. 11 shows images and data from mechanophenotyping H1299 lung cancer cells. Images show that one out of three cancer cells (RICM) in the microscope field of view was able to produce integrin tension (locked tension), indicating the heterogeneity of integrin mechanical activity within H1299 cancer cells. Flow cytometry data of tagged cells indicates that the H1299 cancer cells have two distinct phenotypes when compared to negative controls.

Cell Tagging and Sorting Based on Their Mechanical Activity—Mechanophenotyping Cancer Cells for Metastasis Potential One labeling strategy (FIG. 10) utilizes a horseradish peroxidase (HRP) modified locking strand to selectively hybridize to the mechanically opened hairpin tension probes. Upon addition of HRP substrates, hydrogen peroxide and tyramide-biotin (N-(4-hydroxyphenethyl)-5-((3aS, 4S,6aR)-2-oxohexahydro-1H-thieno[3,4-d]imidazol-4-yl) pentanamide), the membrane proteins within about 20 nm are tagged with biotin moieties. Tyramide contains a phenol group and reacts with proteins that contain the phenol group of the amino acid, tyrosine. The level of tagging depends on the mechano-activity. Cells are collected and the mechanophenotypes can be identified by flow cytometer. A lung cancer cell line H1299 was used as a proof-of-concept system to identify the mechanophenotypes (FIG. 11). The more mechanically active subpopulation could be partially responsible for cancer invasiveness and might be a critical component during cancer metastasis. Identifying and sorting of such subpopulations allows one to perform transcriptomic analysis, and link the phenotype to the genotype, which would further provide potential therapeutic targets for cancer.

Receptor Mechanome Identification

Figure 12:
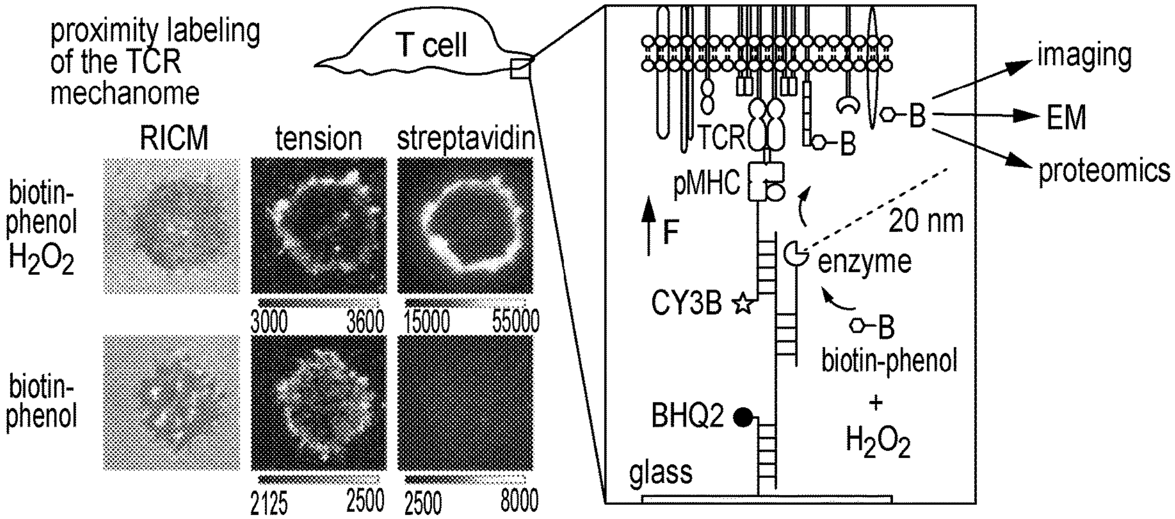
FIG. 12 shows a scheme for use in the identification of the active TCR mechanome.

In T cells understanding such "mechanome" helps illustrate the T cell triggering mechanism. An HRP-functionalized locking strand is selectively hybridized to the mechanically unfolded DNA hairpin tension probe. Proteins within a restricted radius (about less than 20 nm) are tagged and visualized with microscopy upon initiation of enzymatic reaction, thus demonstrating the concept of labeling the TCR mechanome (FIG. 12).

Cancer Vaccine Screening

Figure 13:
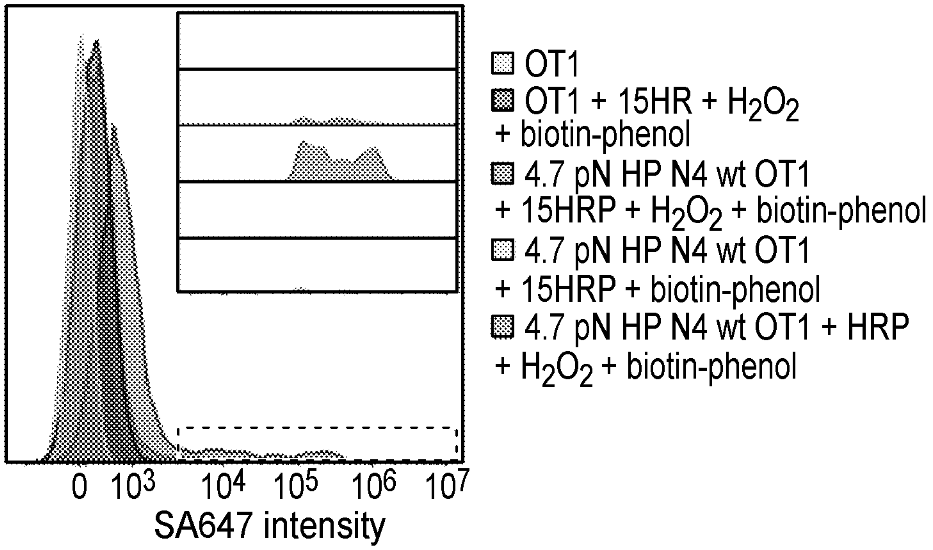
FIG. 13 shows data using OT1 T cells that generated F of greater than 4.7 pN which were tagged and detectable with flow cytometry. Insert shows a zoom-in view of the mechanically active subpopulation from the dashed line box.

The cell mechano-tagging enabled by mechanically selective hybridization could be potentially used for cancer vaccine development, specifically, neoantigen potency evaluation. Since TCR-pMHC mechanics is a readout for antigen potency comparing, mechanics of TCR-pMHC can be used to evaluate the effective activation by neoantigens. Furthermore, this strategy can also be used for identifying and sorting of T cells with TCRs that are specific to identified neoantigens. FIG. 13 shows data on flow cytometry identification of OT1 T cells with the highest mechanical activity against pMHC N4.

Inferring Receptor Bond Force Lifetime With Locking Strategy

Figure 14:
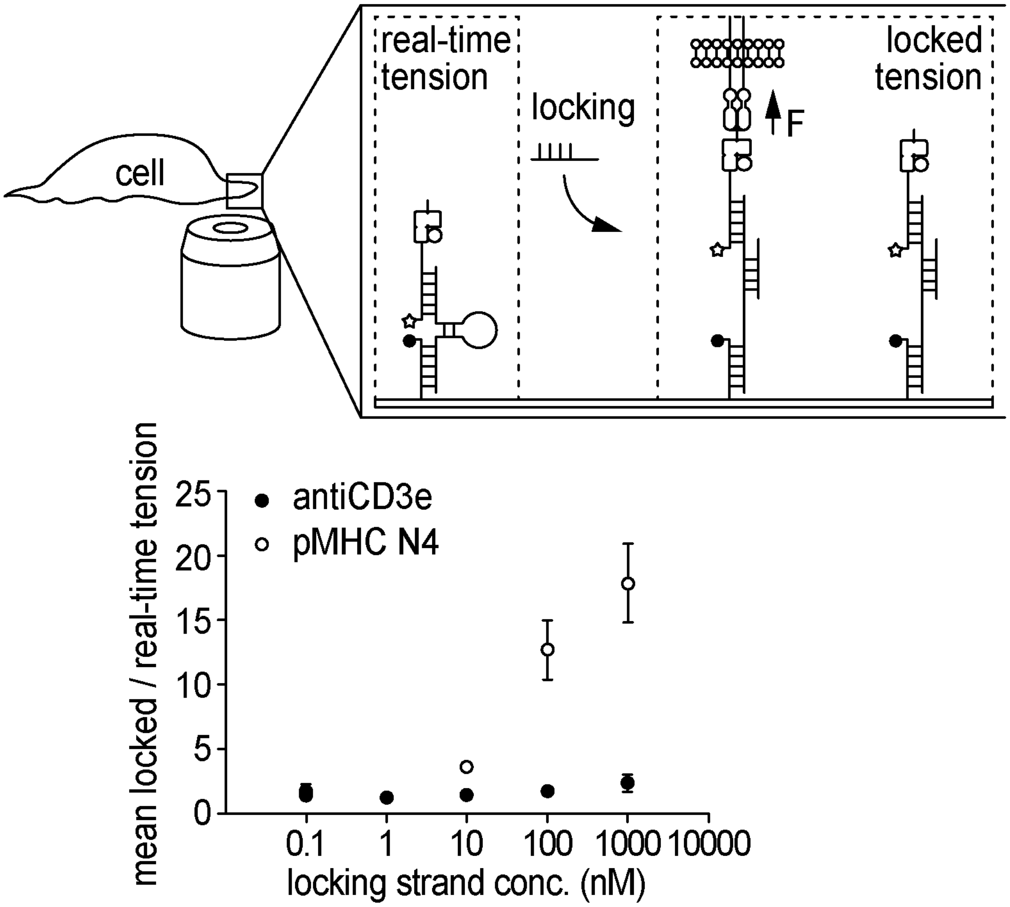
FIG. 14 shows an illustration and data when using a locking strategy to infer TCR-pMHC force lifetime.

The time for locking strand to complete mechanically selective hybridization is relatively shorter than the lifetime of the mechanical event. Thus, at high concentration of locking strand, the vast majority of hairpin unfolding events will lead to lock binding and mechanical information storage; and at low concentrations the locking will fail. Quantitative analysis of the kinetics of locking as a function of locking strand concentration will likely provide an indirect measurement of force lifetimes (τforce) (FIG. 14).

Electrochemical Readout of Cellular Forces

Figure 15:
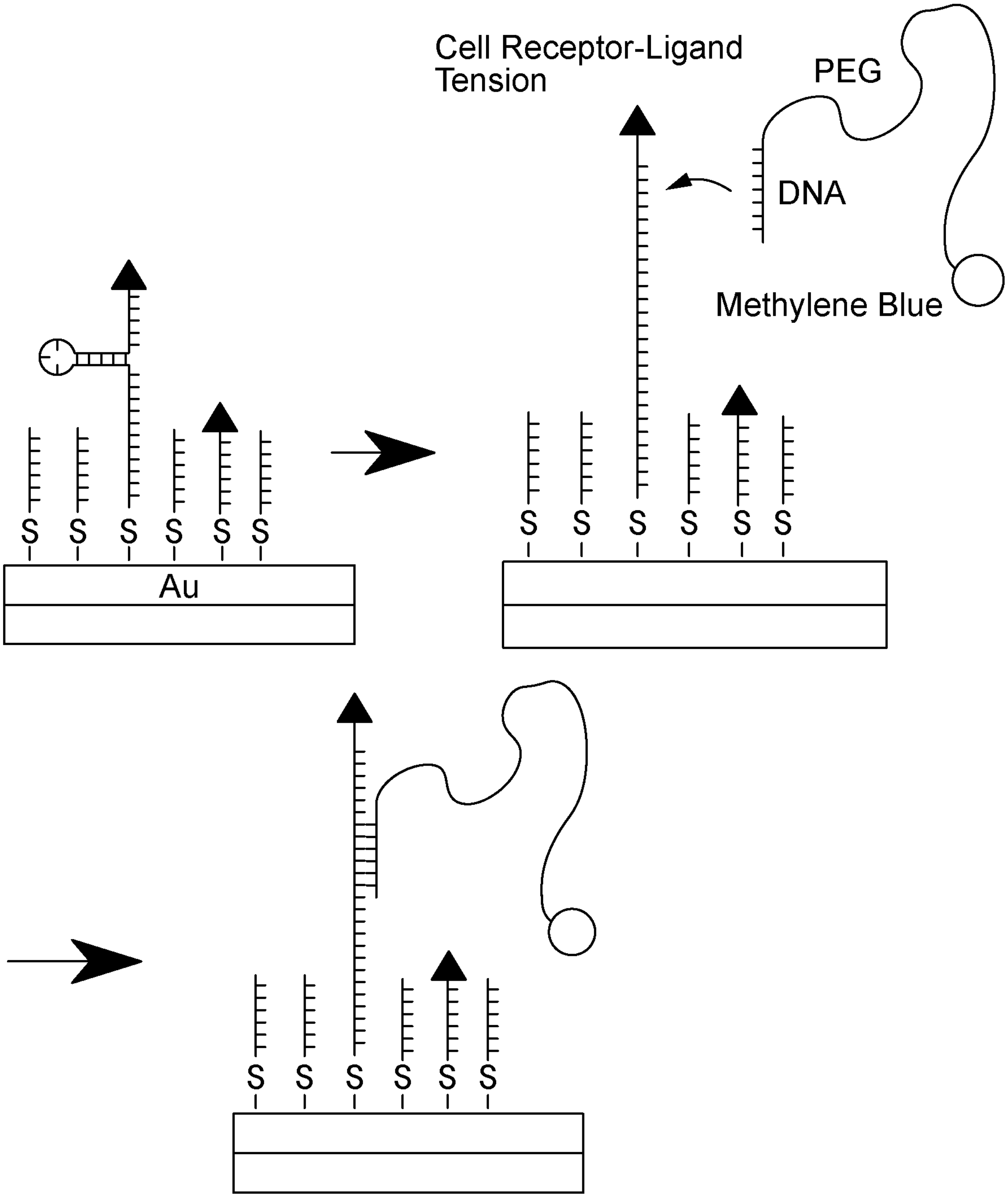
FIG. 15 illustrates a scheme for measuring forces with electrochemical readout.

When DNA hairpin tension probes are immobilized on a substrate coated with gold film, upon addition of locking strand modified with methylene blue, cell integrin-mediated traction forces can be measured by electrochemical readout after the mechanically selective hybridization (FIG. 15). Methylene blue covalently can be attached to DNA through a flexible linker which provides a redox reporter in DNA electrochemistry measurements because intercalated methylene blue is reduced through DNA-mediated charge transport. For example, the incorporation of one or more base mismatches in an oligomer may cause an attenuation of the signal.

The invention claimed is:

1. A system comprising:

a) a device comprising:

i) a peptide ligand;

ii) a nucleic acid complex linker having a first end and a second end, wherein the nucleic acid complex linker is linked to the peptide ligand at the first end;

iii) a surface connected to the nucleic acid complex linker at the second end, wherein the surface is a confined structure;

iv) a quencher conjugated to the nucleic acid complex linker wherein the quencher position remains static when the peptide ligand moves; and v) a first fluorescent molecule conjugated to the nucleic acid complex linker wherein the fluorescent molecule is configured to move its position relative to the quencher when the peptide ligand moves;

wherein the nucleic acid complex linker comprises:

1) a hairpin motif comprising a double stranded stem segment and a single stranded loop segment, 2) a first end tail segment, and 3) a second end tail segment;

wherein the quencher and the first fluorescent molecule are configured to quench when the nucleic acid complex linker is in the form of a hairpin motif; and wherein the quencher and the first fluorescent molecule are not configured to quench when the nucleic acid complex linker is in the form of a single stranded motif; and b) a locking oligonucleotide consisting of SEQ ID NO: 6 that hybridizes with the double stranded stem segment and the single stranded loop segment.

2. The system of claim 1, wherein the locking oligonucleotide is conjugated to a second fluorescent molecule wherein the first fluorescent molecule and second fluorescent molecule have different excitation maximums and/or emission maximums.

3. The system of claim 1, wherein the double stranded stem segment of the hairpin motif comprises SEQ ID NO: 2.

4. The system of claim 1, wherein the single stranded loop segment of the hairpin motif comprises SEQ ID NO: 3.

5. The system of claim 1, wherein the first end tail segment comprises SEQ ID NO: 4.

6. The system of claim 1, wherein the second end tail segment comprises SEQ ID NO: 5.

7. The system of claim 1, wherein the hairpin motif comprises SEQ ID NO: 19.

8. The system of claim 1, wherein the nucleic acid complex linker comprises SEQ ID NO: 1.

9. A system comprising:

a) a device comprising:

i) a peptide ligand;

ii) a nucleic acid complex linker having a first end and a second end, wherein the nucleic acid complex linker is linked to the peptide ligand at the first end;

iii) a surface connected to the nucleic acid complex linker at the second end;

wherein the nucleic acid complex linker comprises 1) a hairpin motif comprising a double stranded stem segment and a single stranded loop segment, 2) a first end tail segment, and 3) a second end tail segment, wherein the surface is a confined structure; and b) a locking oligonucleotide consisting of SEQ ID NO: 6 that hybridizes with the double stranded stem segment and the single stranded loop segment of the hairpin motif when a receptor binds the peptide ligand and unravels the hairpin motif providing an extended form.

10. The system of claim 9, wherein the locking oligonucleotide comprises a label.

* * * * *

SEQUENCE LISTING

<160> NUMBER OF SEQ ID NOS: 24

<210> SEQ ID NO 1
<211> LENGTH: 73
<212> TYPE: DNA
<213> ORGANISM: Artificial
<220> FEATURE:
<223> OTHER INFORMATION: Synthetic construct

<400> SEQUENCE: 1
gtgaaatacc gcacagatgc gtttgtataa atgttttttt catttatact ttaagagcgc 60
cacgtagccc agc 73

<210> SEQ ID NO 2
<211> LENGTH: 9
<212> TYPE: DNA
<213> ORGANISM: Artificial
<220> FEATURE:
<223> OTHER INFORMATION: Synthetic construct

<400> SEQUENCE: 2 gtataaatg 9

<210> SEQ ID NO 3
<211> LENGTH: 7
<212> TYPE: DNA
<213> ORGANISM: Artificial
<220> FEATURE:
<223> OTHER INFORMATION: Synthetic construct

<400> SEQUENCE: 3 ttttttt 7

<210> SEQ ID NO 4
<211> LENGTH: 20
<212> TYPE: DNA
<213> ORGANISM: Artificial
<220> FEATURE:
<223> OTHER INFORMATION: Synthetic construct

<400> SEQUENCE: 4
gtgaaatacc gcacagatgc 20

<210> SEQ ID NO 5
<211> LENGTH: 24
<212> TYPE: DNA
<213> ORGANISM: Artificial
<220> FEATURE:
<223> OTHER INFORMATION: Synthetic construct

<400> SEQUENCE: 5
tttaagagcg ccacgtagcc cagc 24

<210> SEQ ID NO 6
<211> LENGTH: 17
<212> TYPE: DNA
<213> ORGANISM: Artificial
<220> FEATURE:
<223> OTHER INFORMATION: Synthetic construct

<400> SEQUENCE: 6
gaaaaaaaca tttatac 17

<210> SEQ ID NO 7
<211> LENGTH: 24

<212> TYPE: DNA
<213> ORGANISM: Artificial
<220> FEATURE:
<223> OTHER INFORMATION: Synthetic construct

<400> SEQUENCE: 7
cgcatctgtg cggtatttca cttt 24

<210> SEQ ID NO 8
<211> LENGTH: 24
<212> TYPE: DNA
<213> ORGANISM: Artificial
<220> FEATURE:
<223> OTHER INFORMATION: Synthetic construct

<400> SEQUENCE: 8
tttgctgggc tacgtggcgc tctt 24

<210> SEQ ID NO 9
<211> LENGTH: 73
<212> TYPE: DNA
<213> ORGANISM: Artificial
<220> FEATURE:
<223> OTHER INFORMATION: Synthetic construct

<400> SEQUENCE: 9
gtgaaatacc gcacagatgc gtttgtaaat atgtggtggt catatttact ttaagagcgc 60
cacgtagccc agc 73

<210> SEQ ID NO 10
<211> LENGTH: 13
<212> TYPE: DNA
<213> ORGANISM: Artificial
<220> FEATURE:
<223> OTHER INFORMATION: Synthetic construct

<400> SEQUENCE: 10
aaaacattta tac 13

<210> SEQ ID NO 11
<211> LENGTH: 15
<212> TYPE: DNA
<213> ORGANISM: Artificial
<220> FEATURE:
<223> OTHER INFORMATION: Synthetic construct

<400> SEQUENCE: 11
aaaaaacatt tatac 15

<210> SEQ ID NO 12
<211> LENGTH: 21
<212> TYPE: DNA
<213> ORGANISM: Artificial
<220> FEATURE:
<223> OTHER INFORMATION: Synthetic construct

<400> SEQUENCE: 12
aaatgaaaaa aacatttata c 21

<210> SEQ ID NO 13
<211> LENGTH: 25
<212> TYPE: DNA
<213> ORGANISM: Artificial
<220> FEATURE:
<223> OTHER INFORMATION: Synthetic construct

<400> SEQUENCE: 13
gtataaatga aaaaaacatt tatac 25

<210> SEQ ID NO 14
<211> LENGTH: 27
<212> TYPE: DNA
<213> ORGANISM: Artificial
<220> FEATURE:
<223> OTHER INFORMATION: Synthetic construct

<400> SEQUENCE: 14
gtataaatgt ttttttccca gcgtgat 27

<210> SEQ ID NO 15
<211> LENGTH: 25
<212> TYPE: DNA
<213> ORGANISM: Artificial
<220> FEATURE:
<223> OTHER INFORMATION: Synthetic construct

<400> SEQUENCE: 15
gaaaaaaaca tttataccct accta 25

<210> SEQ ID NO 16
<211> LENGTH: 50
<212> TYPE: DNA
<213> ORGANISM: Artificial
<220> FEATURE:
<223> OTHER INFORMATION: Synthetic construct

<400> SEQUENCE: 16
taggtagggt ataaatgttt ttttcgaaaa aaacatttat accctaccta 50

<210> SEQ ID NO 17
<211> LENGTH: 25
<212> TYPE: DNA
<213> ORGANISM: Artificial
<220> FEATURE:
<223> OTHER INFORMATION: Synthetic construct

<400> SEQUENCE: 17
taggtaggca cgctgattag tgtgg 25

<210> SEQ ID NO 18
<211> LENGTH: 25
<212> TYPE: DNA
<213> ORGANISM: Artificial
<220> FEATURE:
<223> OTHER INFORMATION: Synthetic construct

<400> SEQUENCE: 18
ttatcattga cgctgattag tgtgg 25

<210> SEQ ID NO 19
<211> LENGTH: 25
<212> TYPE: DNA
<213> ORGANISM: Artificial
<220> FEATURE:
<223> OTHER INFORMATION: Synthetic construct

<400> SEQUENCE: 19
gtataaatgt ttttttcatt tatac 25

<210> SEQ ID NO 20
<211> LENGTH: 25

-continued

```
<212> TYPE: DNA
<213> ORGANISM: Artificial
<220> FEATURE:
<223> OTHER INFORMATION: Synthetic construct

<400> SEQUENCE: 20

taggtagggt ataaaatgtt ttttc                                            25


<210> SEQ ID NO 21
<211> LENGTH: 8
<212> TYPE: DNA
<213> ORGANISM: Artificial
<220> FEATURE:
<223> OTHER INFORMATION: Synthetic construct

<400> SEQUENCE: 21

taggtagg                                                                8


<210> SEQ ID NO 22
<211> LENGTH: 8
<212> TYPE: PRT
<213> ORGANISM: Artificial
<220> FEATURE:
<223> OTHER INFORMATION: Synthetic construct

<400> SEQUENCE: 22

Ser Ile Ile Asn Phe Glu Lys Leu
1               5


<210> SEQ ID NO 23
<211> LENGTH: 8
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (4)..(4)
<223> OTHER INFORMATION: Xaa can be any naturally occurring amino acid

<400> SEQUENCE: 23

Ser Ile Ile Xaa Phe Glu Lys Leu
1               5


<210> SEQ ID NO 24
<211> LENGTH: 8
<212> TYPE: PRT
<213> ORGANISM: Artificial
<220> FEATURE:
<223> OTHER INFORMATION: Synthetic construct

<400> SEQUENCE: 24

Ser Ile Ile Gly Phe Glu Lys Leu
1               5
```